US012201301B2

(12) United States Patent
Shelton, IV et al.

(10) Patent No.: US 12,201,301 B2
(45) Date of Patent: Jan. 21, 2025

(54) CIRCULAR SURGICAL STAPLER END EFFECTOR HAVING STAPLE LINE ALIGNMENT FEATURE

(71) Applicant: Cilag GmbH International, Zug (CH)

(72) Inventors: Frederick E. Shelton, IV, Hillsboro, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 133 days.

(21) Appl. No.: 17/401,439

(22) Filed: Aug. 13, 2021

(65) Prior Publication Data

US 2023/0049352 A1 Feb. 16, 2023

(51) Int. Cl.
*A61B 17/115* (2006.01)
*A61B 17/064* (2006.01)
*A61B 17/072* (2006.01)
*A61B 17/11* (2006.01)

(52) U.S. Cl.
CPC ....... *A61B 17/1155* (2013.01); *A61B 17/0644* (2013.01); *A61B 2017/07228* (2013.01); *A61B 2017/07264* (2013.01); *A61B 2017/07285* (2013.01); *A61B 17/1114* (2013.01)

(58) Field of Classification Search
CPC ............ A61B 17/1155; A61B 17/0644; A61B 17/1114; A61B 2017/07228; A61B 2017/07264; A61B 2017/07285; A61B 17/115
USPC ........................................ 227/175.1–182.1
See application file for complete search history.

(56) References Cited

U.S. PATENT DOCUMENTS

| | | | |
|---|---|---|---|
| 2,277,931 A | 3/1942 | Moe | |
| 4,047,654 A * | 9/1977 | Alvarado | A61B 17/115 227/19 |
| 4,407,286 A | 10/1983 | Noiles et al. | |
| 4,505,273 A | 3/1985 | Braun et al. | |
| 4,669,647 A | 6/1987 | Storace | |
| 4,848,328 A | 7/1989 | Laboureau et al. | |

(Continued)

FOREIGN PATENT DOCUMENTS

| | | |
|---|---|---|
| EP | 1875870 A1 | 1/2008 |
| EP | 2157918 A1 | 3/2010 |

(Continued)

OTHER PUBLICATIONS

U.S. Appl. No. 17/401,391, entitled, "Methods of Forming an Anastomosis Between Organs with an Expandable Pattern," filed Aug. 13, 2021.

(Continued)

*Primary Examiner* — Robert F Long
(74) *Attorney, Agent, or Firm* — Frost Brown Todd LLP

(57) ABSTRACT

A surgical stapler for creating an anastomosis includes a stapling head assembly having a deck member that incorporates an alignment feature. The alignment feature aligns with a transection staple line prior to creating the anastomosis. In some versions the alignment feature is a groove formed in a surface of the deck member. The surgical stapler may include an anvil with a complementary stepped feature to the alignment feature of the deck member. Various surgical staplers with an alignment feature can be oval shaped, circular shaped, or dog-bone shaped. In some versions different staple geometries are used along the deck member incorporating the alignment feature.

18 Claims, 18 Drawing Sheets

(56) References Cited

U.S. PATENT DOCUMENTS

| | | | |
|---|---|---|---|
| 4,874,122 A | 10/1989 | Froelich et al. | |
| 4,899,745 A | 2/1990 | Laboureau et al. | |
| 5,292,053 A | 3/1994 | Bilotti et al. | |
| 5,309,927 A | 5/1994 | Welch | |
| 5,333,773 A | 8/1994 | Main et al. | |
| 5,342,396 A | 8/1994 | Cook | |
| 5,350,104 A | 9/1994 | Main et al. | |
| 5,425,489 A | 6/1995 | Shichman et al. | |
| 5,533,661 A | 7/1996 | Main et al. | |
| 5,713,505 A * | 2/1998 | Huitema | A61B 17/07207 227/176.1 |
| 5,725,554 A | 3/1998 | Simon et al. | |
| 5,732,872 A | 3/1998 | Bolduc et al. | |
| 5,993,468 A | 11/1999 | Rygaard | |
| 6,352,541 B1 | 3/2002 | Kienzle et al. | |
| 6,425,903 B1 | 7/2002 | Voegele | |
| 6,616,686 B2 | 9/2003 | Coleman et al. | |
| 6,629,630 B2 | 10/2003 | Adams | |
| 6,767,356 B2 | 7/2004 | Kanner et al. | |
| 6,769,590 B2 | 8/2004 | Vresh et al. | |
| 6,915,937 B2 | 7/2005 | Lat et al. | |
| 7,056,330 B2 | 6/2006 | Gayton | |
| 7,422,138 B2 * | 9/2008 | Bilotti | A61B 17/115 227/19 |
| 7,722,643 B2 | 5/2010 | Schaller et al. | |
| 7,824,426 B2 | 11/2010 | Racenet et al. | |
| 7,934,630 B2 | 5/2011 | Shelton, IV et al. | |
| 8,143,870 B2 | 3/2012 | Ng et al. | |
| 8,267,301 B2 * | 9/2012 | Milliman | A61B 17/115 227/176.1 |
| 8,328,063 B2 | 12/2012 | Milliman et al. | |
| 8,413,870 B2 | 4/2013 | Pastorelli et al. | |
| 8,613,384 B2 * | 12/2013 | Pastorelli | A61B 17/072 227/179.1 |
| 8,789,738 B2 | 7/2014 | Knodel et al. | |
| 8,801,732 B2 | 8/2014 | Harris et al. | |
| 8,910,847 B2 * | 12/2014 | Nalagatla | H04B 7/0682 227/19 |
| 8,978,954 B2 | 3/2015 | Shelton, IV et al. | |
| 9,016,541 B2 | 4/2015 | Viola et al. | |
| 9,113,885 B2 * | 8/2015 | Hodgkinson | A61B 17/068 |
| 9,192,387 B1 * | 11/2015 | Holsten | A61B 17/32053 |
| 9,265,500 B2 | 2/2016 | Sorrentino et al. | |
| 9,402,628 B2 | 8/2016 | Beardsley | |
| 9,713,469 B2 | 7/2017 | Leimbach et al. | |
| 9,782,171 B2 * | 10/2017 | Viola | A61B 17/1155 |
| 9,848,874 B2 | 12/2017 | Kostrzewski | |
| 9,907,552 B2 | 3/2018 | Measamer et al. | |
| 9,936,949 B2 | 4/2018 | Measamer et al. | |
| 10,080,565 B2 * | 9/2018 | Pastorelli | A61B 17/068 |
| 10,105,134 B2 | 10/2018 | Biedermann et al. | |
| 10,130,359 B2 | 11/2018 | Hess et al. | |
| 10,166,026 B2 | 1/2019 | Shelton, IV et al. | |
| 10,285,705 B2 | 5/2019 | Shelton, IV et al. | |
| 10,327,776 B2 | 6/2019 | Harris et al. | |
| 10,639,040 B2 | 5/2020 | Penna et al. | |
| 10,709,452 B2 | 7/2020 | DiNardo et al. | |
| 10,856,867 B2 | 12/2020 | Shelton, IV et al. | |
| 10,925,607 B2 | 2/2021 | Penna et al. | |
| 11,147,559 B2 | 10/2021 | Wise et al. | |
| 11,241,232 B2 | 2/2022 | Guerrera | |
| 11,284,890 B2 | 3/2022 | Nalagatla et al. | |
| 11,291,450 B2 | 4/2022 | Nalagatla et al. | |
| 11,523,821 B2 | 12/2022 | Harris et al. | |
| 2003/0009193 A1 * | 1/2003 | Corsaro | A61B 17/29 227/175.1 |
| 2003/0178465 A1 * | 9/2003 | Bilotti | A61B 17/115 227/180.1 |
| 2004/0073237 A1 | 4/2004 | Leinsing | |
| 2006/0291981 A1 | 12/2006 | Viola et al. | |
| 2008/0082126 A1 | 4/2008 | Murray et al. | |
| 2008/0294179 A1 * | 11/2008 | Balbierz | A61B 17/10 606/151 |
| 2009/0001122 A1 * | 1/2009 | Prommersberger | A61B 17/07292 227/176.1 |
| 2009/0188964 A1 * | 7/2009 | Orlov | A61F 2/2445 227/176.1 |
| 2010/0108740 A1 * | 5/2010 | Pastorelli | A61B 17/115 227/176.1 |
| 2010/0108741 A1 * | 5/2010 | Hessler | A61B 17/068 227/179.1 |
| 2010/0191262 A1 | 7/2010 | Harris et al. | |
| 2010/0213240 A1 * | 8/2010 | Kostrzewski | A61B 17/3209 227/180.1 |
| 2011/0011916 A1 * | 1/2011 | Levine | A61B 17/115 227/179.1 |
| 2011/0017800 A1 * | 1/2011 | Viola | A61B 17/115 227/175.1 |
| 2012/0080498 A1 | 4/2012 | Shelton, IV et al. | |
| 2012/0116379 A1 * | 5/2012 | Yates | A61B 34/25 606/33 |
| 2012/0193395 A1 * | 8/2012 | Pastorelli | A61B 17/1114 227/176.1 |
| 2012/0325893 A1 * | 12/2012 | Pastorelli | A61B 17/115 227/177.1 |
| 2013/0168433 A1 * | 7/2013 | Kostrzewski | A61B 17/068 227/175.1 |
| 2013/0214027 A1 * | 8/2013 | Hessler | A61B 17/068 227/175.1 |
| 2014/0027493 A1 * | 1/2014 | Jankowski | A61B 17/105 227/176.1 |
| 2014/0158747 A1 | 6/2014 | Measamer et al. | |
| 2015/0083772 A1 | 3/2015 | Miller et al. | |
| 2015/0289872 A1 * | 10/2015 | Chen | A61B 17/068 227/179.1 |
| 2016/0000428 A1 * | 1/2016 | Scirica | A61B 17/068 227/180.1 |
| 2016/0278768 A1 | 9/2016 | Johnson et al. | |
| 2017/0027610 A1 * | 2/2017 | Cabrera | A61B 17/3496 |
| 2017/0086833 A1 * | 3/2017 | Eckert | A61B 17/068 |
| 2017/0119397 A1 | 5/2017 | Harris et al. | |
| 2017/0231629 A1 * | 8/2017 | Stopek | A61B 17/07207 227/176.1 |
| 2017/0281172 A1 * | 10/2017 | Shelton, IV | A61B 17/1155 |
| 2017/0333064 A1 * | 11/2017 | Ebner | A61B 17/285 |
| 2018/0132849 A1 | 5/2018 | Miller et al. | |
| 2018/0132854 A1 * | 5/2018 | Miller | A61B 17/1114 |
| 2018/0235616 A1 * | 8/2018 | Shelton, IV | A61B 17/07292 |
| 2018/0235635 A1 | 8/2018 | Rekstad et al. | |
| 2018/0242974 A1 | 8/2018 | Guerrera et al. | |
| 2018/0325508 A1 * | 11/2018 | Aronhalt | A61B 17/068 |
| 2019/0000481 A1 * | 1/2019 | Harris | A61B 17/3468 |
| 2019/0328394 A1 * | 10/2019 | Williams | A61B 17/064 |
| 2020/0038017 A1 | 2/2020 | Hess et al. | |
| 2020/0054339 A1 | 2/2020 | Scirica et al. | |
| 2020/0229814 A1 | 7/2020 | Amariglio et al. | |
| 2021/0290225 A1 * | 9/2021 | Shi | A61B 17/1155 |
| 2023/0045940 A1 * | 2/2023 | Shelton, IV | A61B 17/1155 |
| 2023/0047471 A1 * | 2/2023 | Jones | A61B 17/1155 |
| 2023/0048389 A1 | 2/2023 | Bruce et al. | |
| 2023/0049242 A1 | 2/2023 | Jones et al. | |
| 2023/0049352 A1 * | 2/2023 | Shelton, IV | A61B 17/1155 |
| 2023/0051305 A1 | 2/2023 | Jones et al. | |
| 2023/0051659 A1 | 2/2023 | Boudreaux et al. | |
| 2023/0053080 A1 * | 2/2023 | Jones | A61B 17/0644 |
| 2023/0102965 A1 * | 3/2023 | Wise | A61B 17/1155 227/175.1 |

FOREIGN PATENT DOCUMENTS

| | | |
|---|---|---|
| EP | 2649949 A1 | 10/2013 |
| EP | 3225176 A1 | 10/2017 |
| EP | 3225179 A1 | 10/2017 |
| EP | 3245958 A1 | 11/2017 |
| EP | 3130292 B1 | 8/2018 |
| EP | 3173030 B1 | 10/2019 |
| EP | 3643252 A1 | 4/2020 |
| WO | WO 2001/054594 A1 | 8/2001 |
| WO | WO 2002/009595 A1 | 2/2002 |

(56) References Cited

FOREIGN PATENT DOCUMENTS

| WO | WO-0209595 A1 | * | 2/2002 | ........... A61B 17/115 |
| WO | WO 2005/115254 A2 | | 12/2005 | |
| WO | WO 2008/141288 A1 | | 11/2008 | |
| WO | WO-2012072138 A1 | * | 6/2012 | ......... A61B 17/1155 |
| WO | WO 2020/249487 A1 | | 12/2020 | |

OTHER PUBLICATIONS

U.S. Appl. No. 17/401,428, entitled, "Staple Forming Features for Circular Surgical Stapler," filed Aug. 13, 2021.
U.S. Appl. No. 17/401,430, entitled, "Non-Circular End Effector Features for Surgical Stapler," filed Aug. 13, 2021.
U.S. Appl. No. 17/401,444, entitled, "Circular Surgical Stapler for Forming Pattern of Non-Tangential Staples," filed Aug. 13, 2021.
U.S. Appl. No. 17/401,451, entitled, "Circular Surgical Stapler Having Staples with Expandable Crowns," filed Aug. 13, 2021.
U.S. Appl. No. 17/401,460, entitled, "Circular Surgical Stapler for Forming Cross-Pattern of Staples," filed Aug. 13, 2021.
International Search Report and Written Opinion dated Nov. 14, 2022, for International Application No. PCT/IB2022/057444, 12 pages.
International Search Report and Written Opinion dated Jan. 27, 2023, for International Application No. PCT/IB2022/057446, 19 pages.
International Search Report and Written Opinion dated Nov. 23, 2022, for International Application No. PCT/IB2022/057449, 15 pages.
International Search Report and Written Opinion dated Jan. 25, 2023, for International Application No. PCT/IB2022/057442, 20 pages.
International Search Report and Written Opinion dated Nov. 14, 2022, for International Application No. PCT/IB2022/057443, 12 pages.
International Search Report and Written Opinion dated Nov. 24, 2022, for International Application No. PCT/IB2022/057451, 13 pages.

* cited by examiner

CIRCULAR SURGICAL STAPLER END EFFECTOR HAVING STAPLE LINE ALIGNMENT FEATURE

BACKGROUND

A circular surgical stapler may be used to form an anastomosis between two organ portions of a patient's digestive tract. Examples of circular surgical staplers are described in U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; U.S. Pub. No. 2018/0132849, entitled "Staple Forming Pocket Configurations for Circular Surgical Stapler Anvil," published May 17, 2018, now abandoned; and U.S. Pat. No. 10,709,452, entitled "Methods and Systems for Performing Circular Stapling," issued Jul. 14, 2020. The disclosure of each of the above-cited U.S. Patent Publications and U.S. Patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
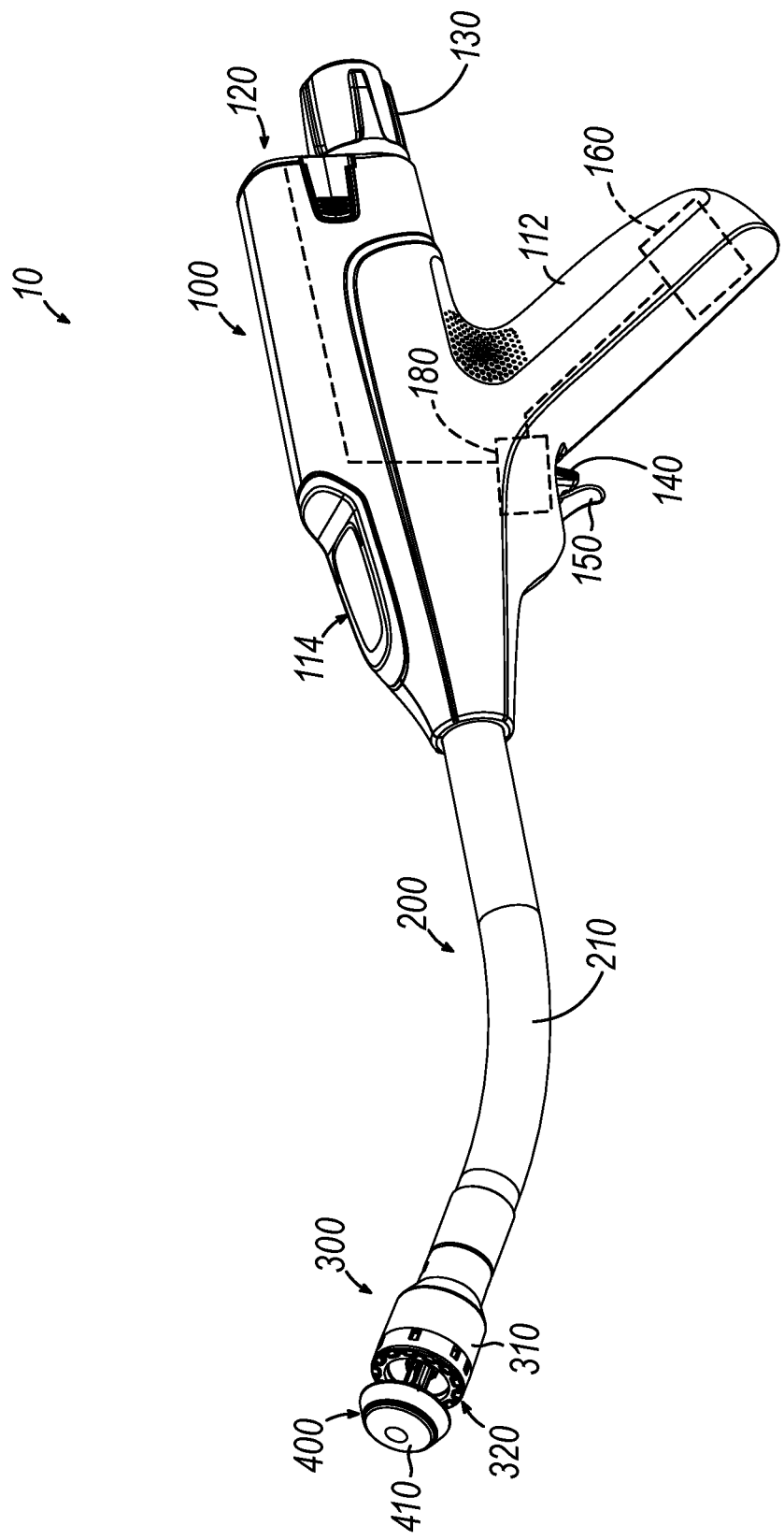
FIG. 1 depicts a perspective view of an exemplary circular surgical stapler that includes a handle assembly, a shaft assembly, and an end effector having a stapling head assembly and an anvil.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. Overview of Exemplary Circular Surgical Stapling Instrument

Figure 2:
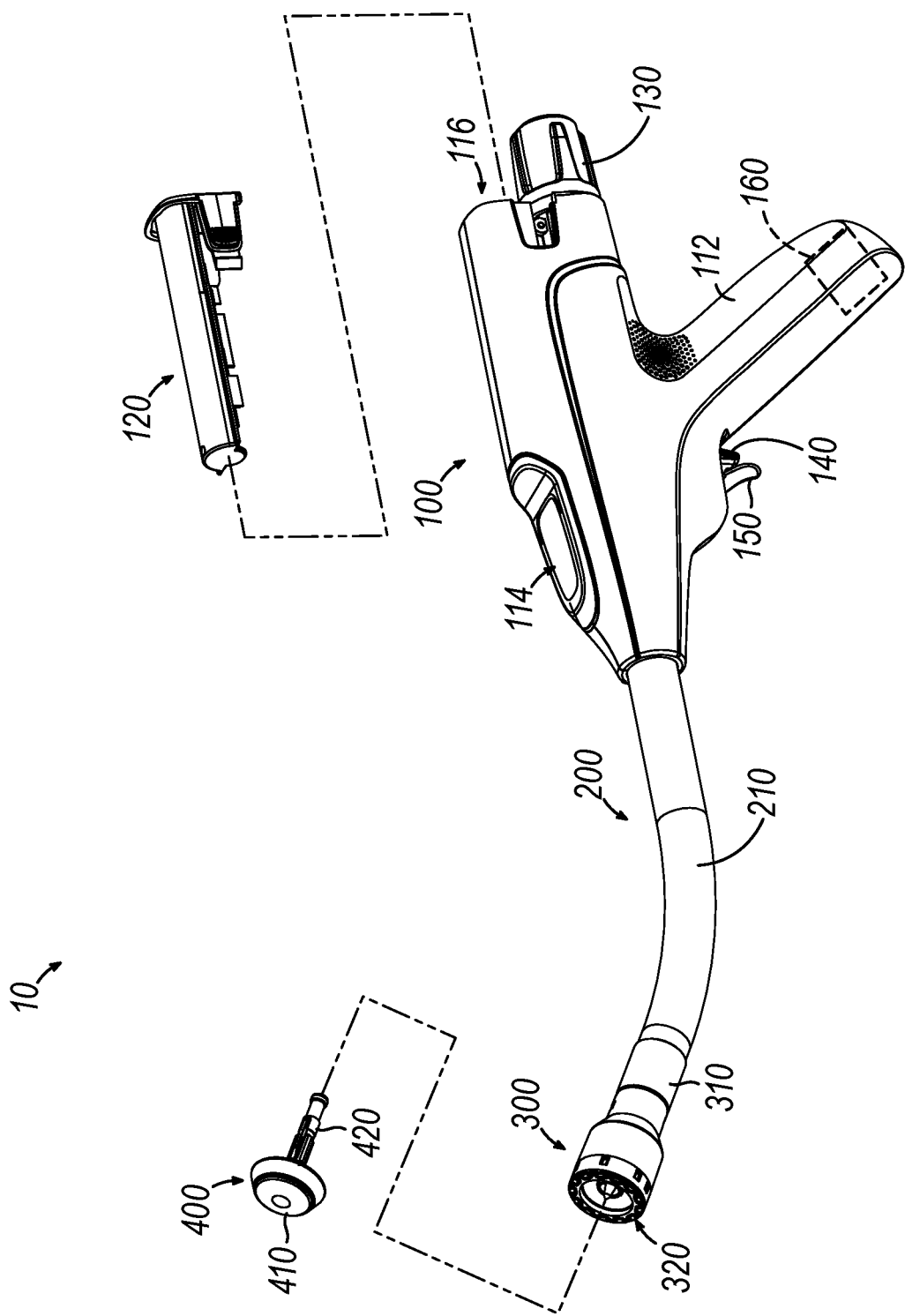
FIG. 2 depicts a perspective view of the circular stapler of FIG. 1, with a battery pack removed from the handle assembly and the anvil separated from the stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly in the form of a handle assembly (100), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A rotatable knob (130) at the proximal end of handle assembly (100) is rotatable to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the clamped tissue.

A. Exemplary Anvil

Figure 3:
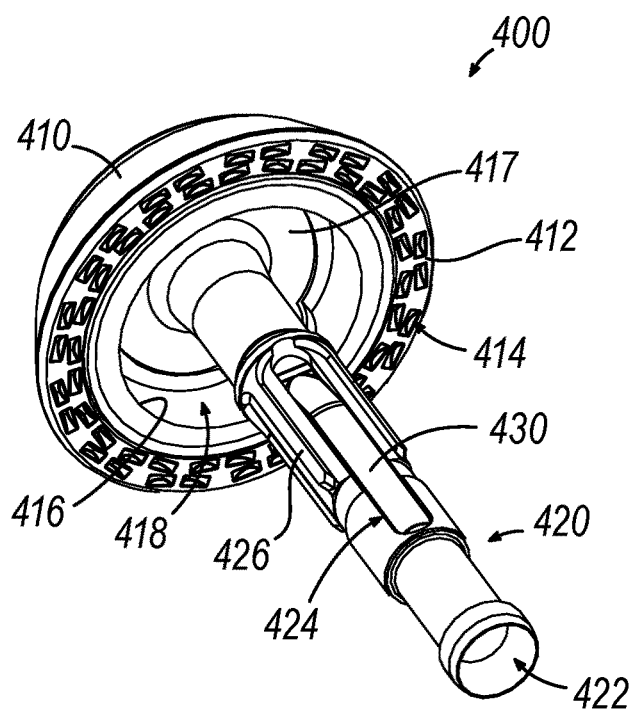
FIG. 3 depicts a perspective view of the anvil of the circular stapler of FIG. 1.

As best seen in FIG. 3, anvil (400) of the present example comprises a head (410) and a shank (420). Head (410) includes a proximal stapling surface (412) that defines a plurality of staple forming pockets (414). Staple forming pockets (414) are arranged in two concentric annular arrays in the present example. Staple forming pockets (414) are configured to deform staples as the staples are driven into staple forming pockets (414). Proximal stapling surface (412) terminates at an inner edge (416), which defines an outer boundary of an annular recess (418) surrounding shank (420). A breakable washer (417) is positioned within annular recess (418) and is configured to provide the operator with a tactile and audible indication that a distal firing stroke has been completed, in addition to serving as a cutting board, as described in greater detail below.

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Latch members (430) thus act as retaining clips. This allows anvil (400) to be removably secured to an actuatable closure member in the form of a trocar (330) of stapling head assembly (300), as will be described in greater detail below. Shank (420) of anvil (400) and trocar (330) of stapling head assembly (300) thus cooperate with one another as coupling members.

B. Exemplary Stapling Head Assembly

Figure 4:
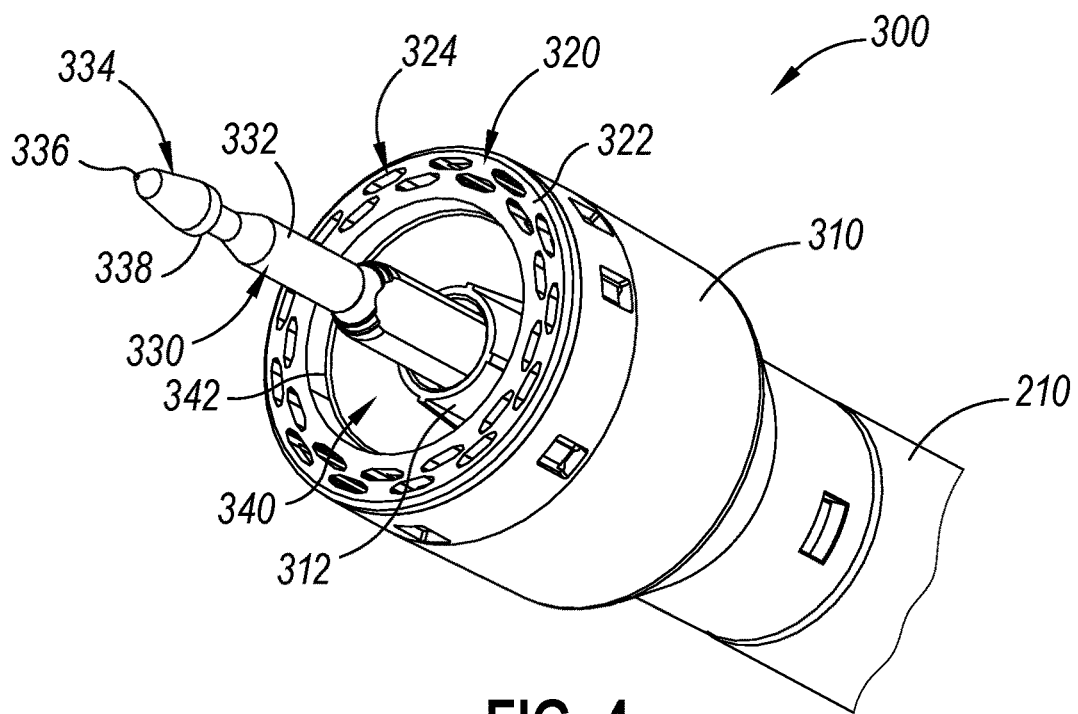
FIG. 4 depicts a perspective view of the stapling head assembly of the circular stapler of FIG. 1.
Figure 5:
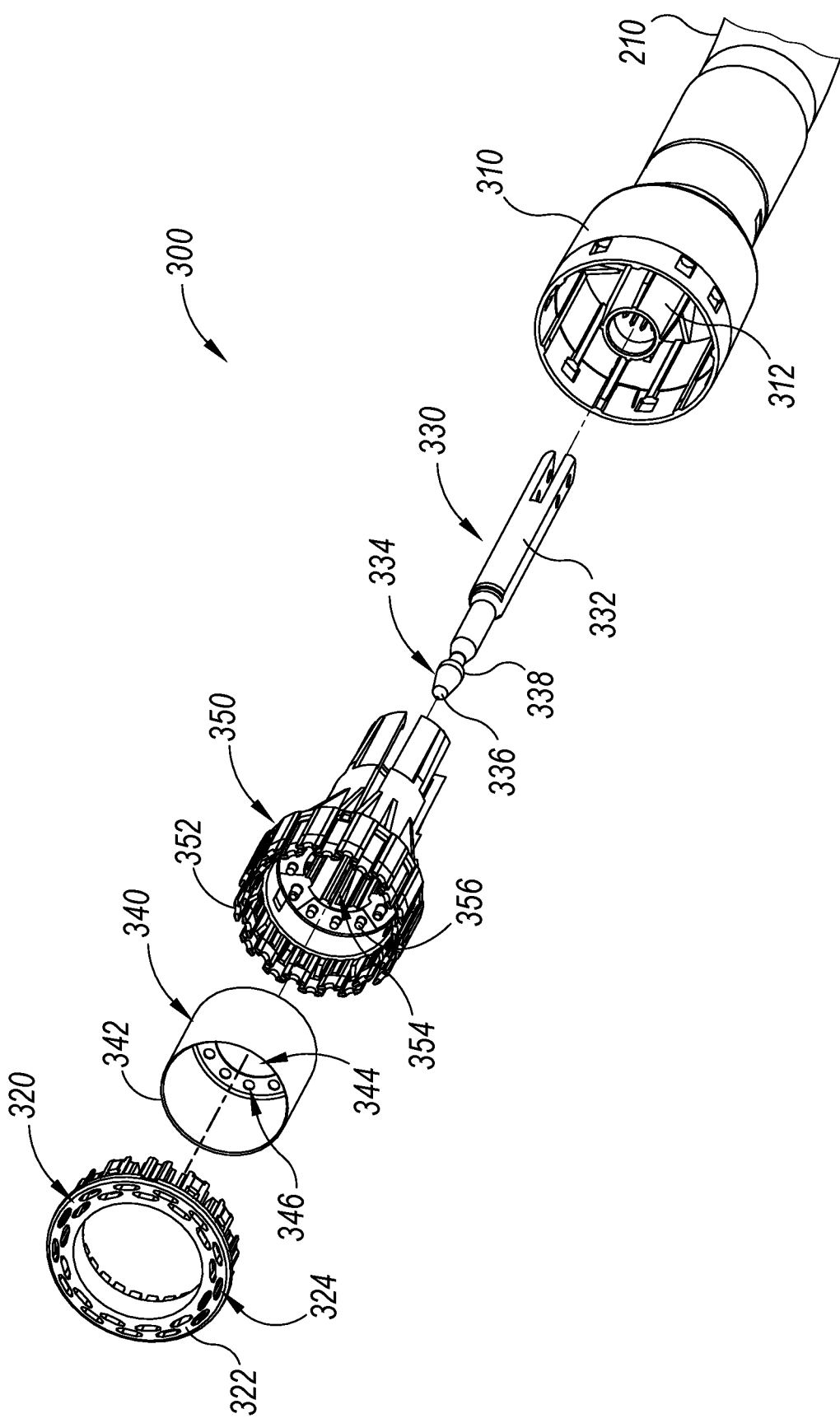
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a tubular body member (310) and a staple driver member (350) slidably housed therein. Body member (310) includes a distally extending cylindraceous inner core member (312) positioned coaxially therein. Body member (310) is fixedly secured to an outer sheath (210) of shaft assembly (200), and body member (310) and outer sheath (210) thus serve together as a mechanical ground for stapling head assembly (300).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and a radially inwardly extending proximal surface (338). Head (334) and the distal portion of shaft (332) are configured for insertion into bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. As shown best in FIG. 5, staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple distally into a corresponding staple forming pocket (414) when stapling head assembly (300) is actuated (or "fired"). Staple driver member (350) also defines a bore (354) that is configured to coaxially and slidably receive core member (312) of body member (310). An annular array of studs (356) project distally from a distally presented surface surrounding bore (354).

A cylindraceous knife member (340) is coaxially positioned within a distally-opening central recess of staple driver member (350) that communicates with bore (354). Knife member (340) includes a distally presented, sharp circular cutting edge (342). Knife member (340) is sized such that knife member (340) defines an outer diameter that is just smaller than the diameter defined by the radially inner-most surfaces of the inner annular array of staple drivers (352). Knife member (340) also defines a central opening that is configured to coaxially receive core member (312) of body member (310). An annular array of openings (346) formed in knife member (340) is configured to mate with the annular array of studs (356) of staple driver member (350), such that knife member (340) is fixedly secured to staple driver member (350) via studs (356) and openings (346).

Figure 9:
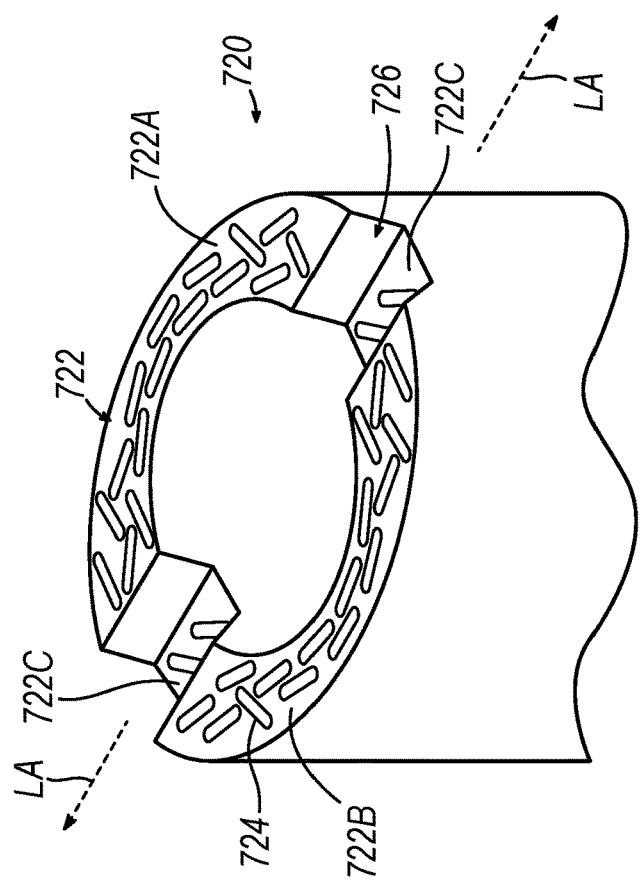
FIG. 9 depicts a perspective view of the annular deck member of the stapling head assembly of FIG. 8.

An annular deck member (320) is fixedly secured to a distal end of body member (310). Deck member (320) includes a distally presented stapling surface in the form of a deck surface (322) having two concentric annular arrays of staple openings (324). Staple openings (324) are arranged to align with the arrangement of staple drivers (352) of staple driver member (350) and staple forming pockets (414) of anvil (400) described above. Each staple opening (324) is configured to slidably receive and provide a pathway for a corresponding staple driver (352) to drive a corresponding staple distally through deck member (320) and into a corresponding staple forming pocket (414) when stapling head assembly (300) is actuated. As best seen in FIG. 9, deck member (320) has a central opening that defines an inner diameter that is just slightly larger than the outer diameter defined by knife member (340). Deck member (320) is thus configured to permit knife member (340) to translate longitudinally through the central opening concurrently with longitudinal translation of staple driver member (350). In particular, knife member (340) is configured to actuate relative to deck member (340) between a proximal retracted position and a distal extended position, where cutting edge (342) is proximal to deck surface (322) in the proximal retracted position and distal to deck surface (322) in the distal extended position.

C. Exemplary Shaft Assembly

Figure 6:
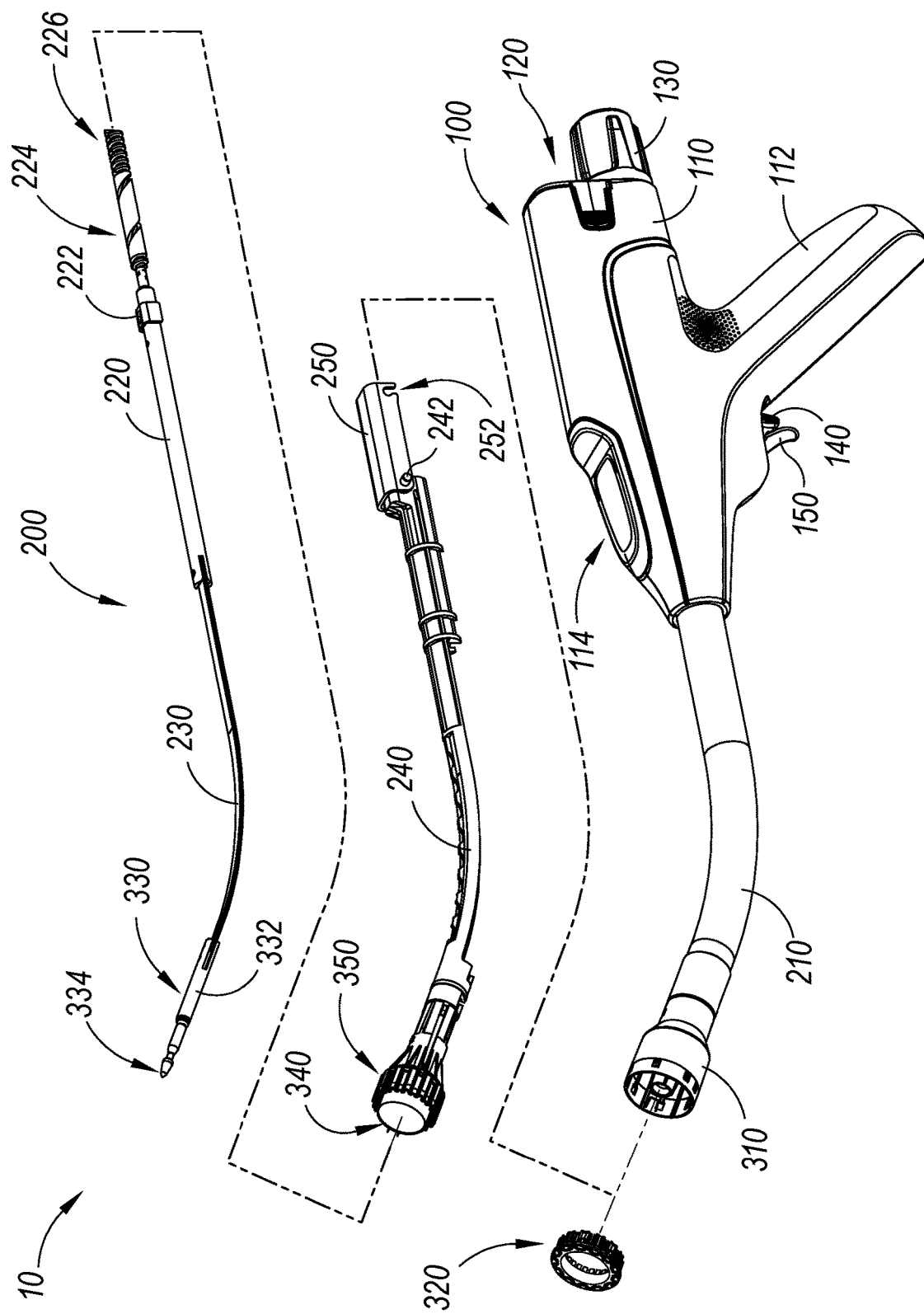
FIG. 6 depicts an exploded perspective view of the circular stapler of FIG. 1, with portions of the shaft assembly shown separated from each other.

FIG. 6 shows various components of shaft assembly (200), which operatively couple components of stapling head assembly (300) with components of handle assembly (100). In particular, and as noted above, shaft assembly (200) includes an outer sheath (210) that extends between handle assembly (100) and body member (310) and includes a medial portion that extends along a curved path.

Shaft assembly (200) further includes a trocar actuation rod (220) having a proximal end operatively coupled with rotatable knob (130) and a distal end coupled with a flexible trocar actuation band assembly (230), the assembly of which is slidably housed within outer sheath (210). The distal end of trocar actuation band assembly (230) is fixedly secured to the proximal end of trocar shaft (332), such that trocar (330) will translate longitudinally relative to outer sheath (210) in response to translation of trocar actuation band assembly (230) and trocar actuation rod (220) relative to outer sheath (210), which occurs in response to rotation of rotatable knob (130). A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a section of coarse helical threading (224) and a section of fine helical threading (226) proximal to coarse helical threading (224), which are configured to control a rate of longitudinal advancement of trocar actuation rod (220), as described in greater detail below.

Shaft assembly (200) further includes a stapling head assembly driver (240) that is slidably housed within outer sheath (210) and about the combination of trocar actuation rod (220) and trocar actuation band assembly (230). Stapling head assembly driver (240) includes a distal end that is fixedly secured to the proximal end of staple driver member (350), a proximal end secured to a drive bracket (250) via a pin (242), and a flexible section disposed therebetween. It should therefore be understood that staple driver member (350) will translate longitudinally relative to outer sheath (210) in response to translation of stapling head assembly driver (240) and drive bracket (250) relative to outer sheath (210).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and releasably receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140), a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, and then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) proximally toward stapling head assembly (300); and in a second angular direction (e.g., counterclockwise) to extend anvil (400) distally away from stapling head assembly (300). Knob (130) may thus be used to adjust a gap distance (d) between opposing stapling surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300) to staple and cut tissue clamped between anvil (400) and stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) is operable to actuate a switch of motor activation module (180) (FIG. 1) when firing trigger (150) is pivoted proximally to a fired position. Motor activation module (180) is in communication with battery pack (120) and motor (160), such that motor activation module (180) is configured to provide activation of motor (160) with electrical power from battery pack (120) in response to firing trigger (150) actuating the switch of motor activation module (180). Thus, motor (160) will be activated when firing trigger (150) is pivoted. This activation of motor (160) will actuate stapling head assembly (300) via drive bracket (250), as described in greater detail below.

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, colon, or other portions of the patient's digestive tract, or any other tubular anatomical structures.

Figure 7A:
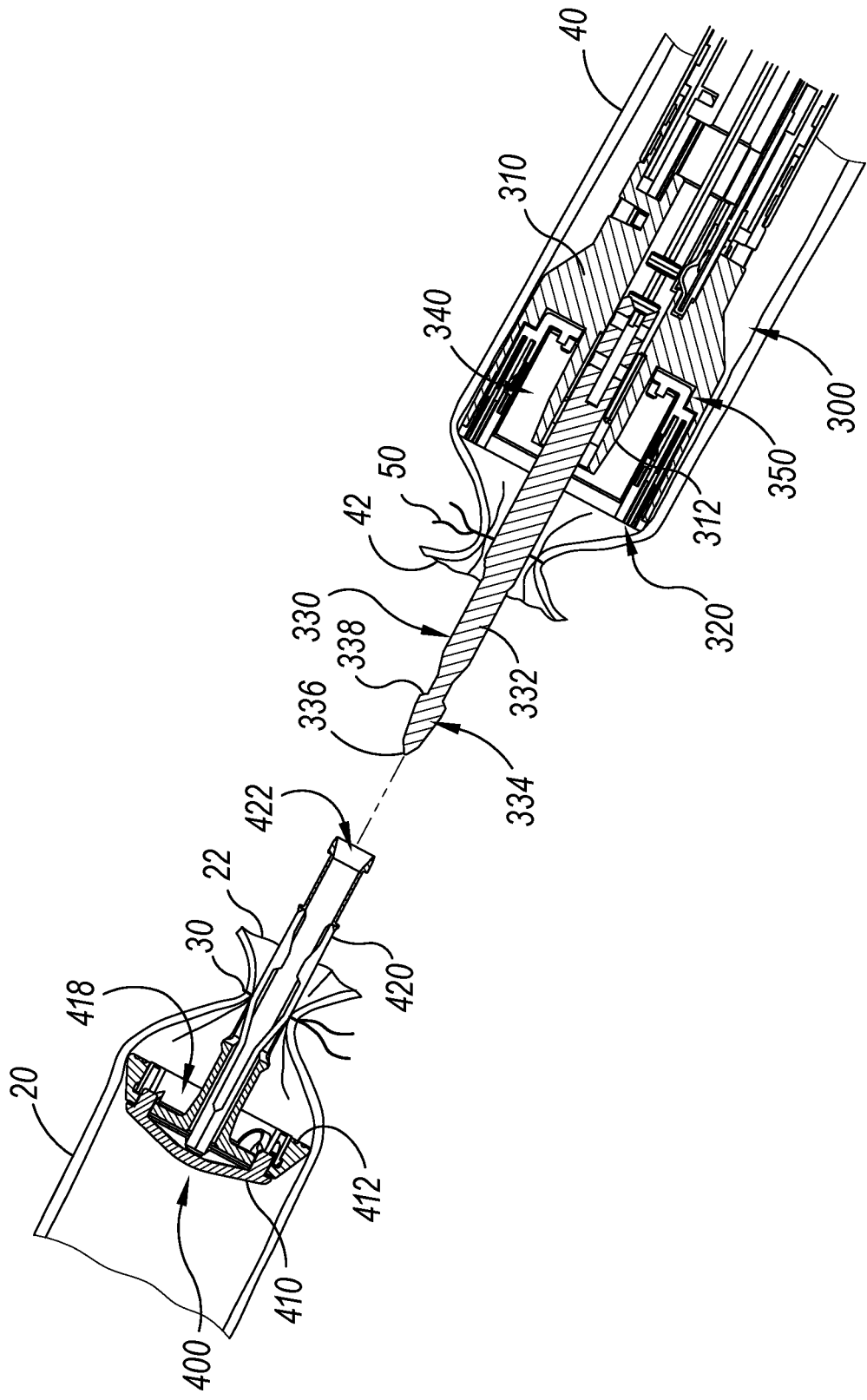
FIG. 7A depicts a cross-sectional side view of the anvil of FIG. 3 positioned within a first section of a digestive tract and the stapling head assembly of FIG. 4 positioned within a separate second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). Stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
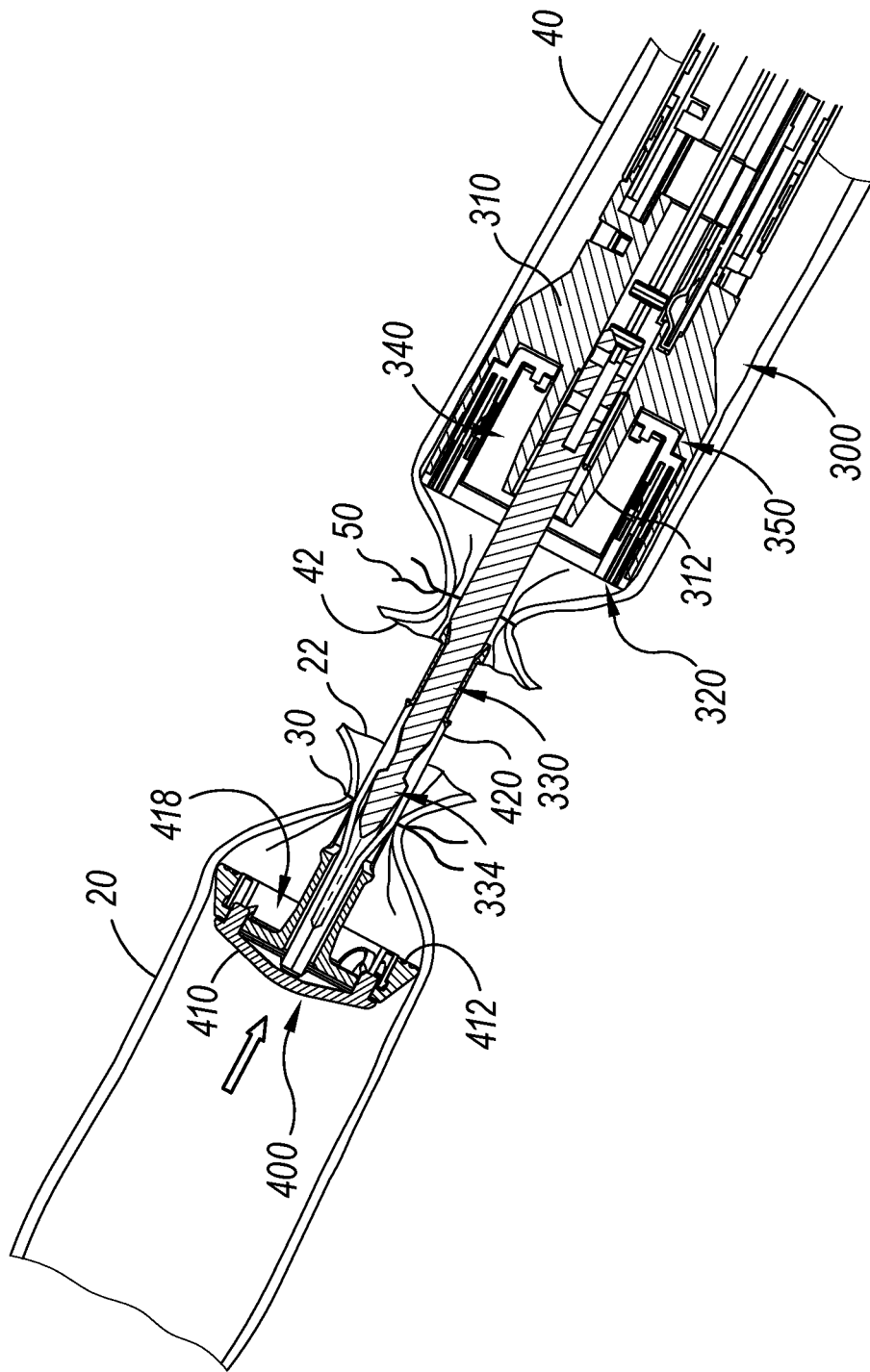
FIG. 7B depicts a cross-sectional side view of the anvil of FIG. 3 positioned within the first section of the digestive tract and the stapling head assembly of FIG. 4 positioned within the separate second section of the digestive tract, with the anvil secured to the stapling head assembly.
Figure 7C:
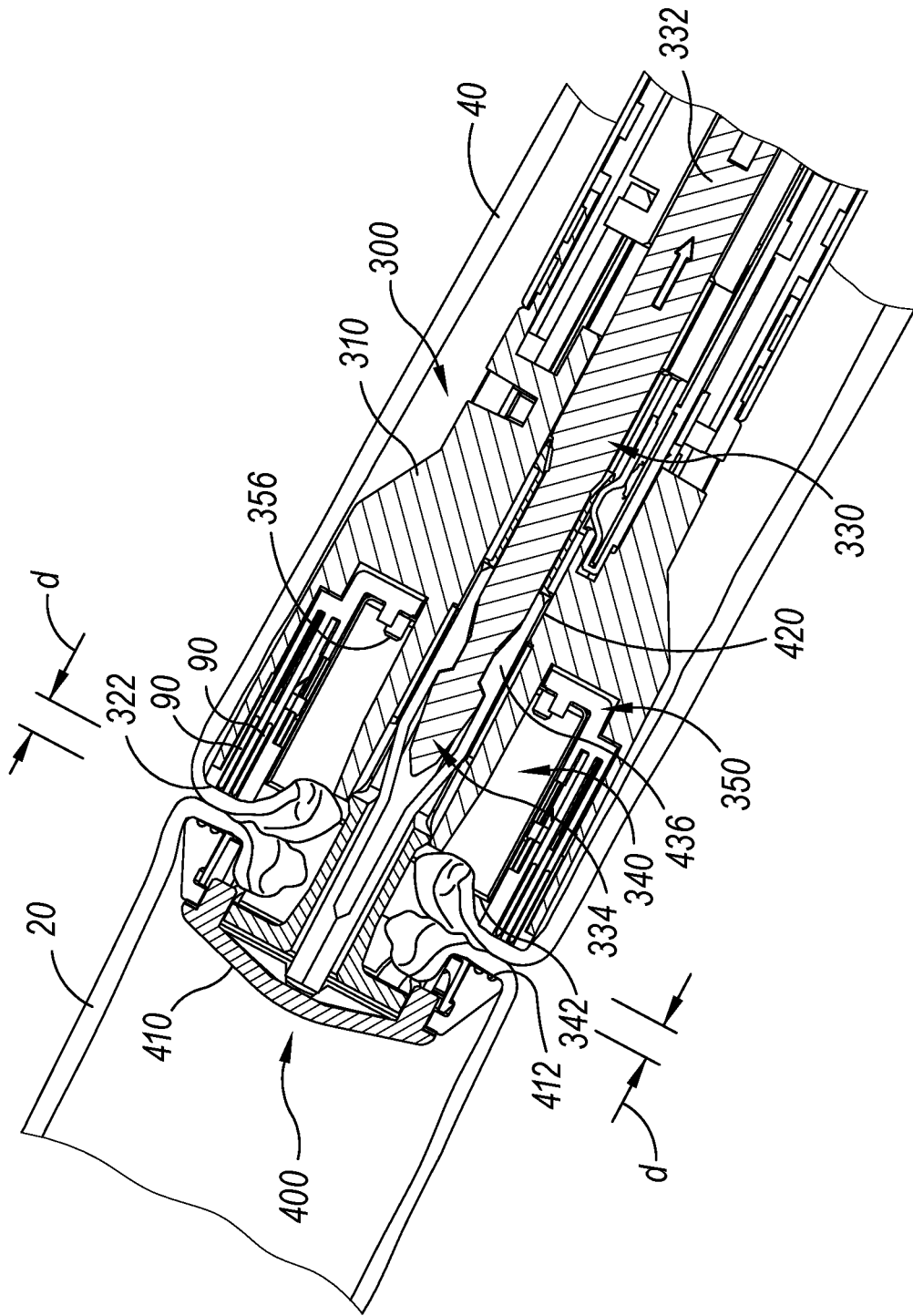
FIG. 7C depicts a cross-sectional side view of the anvil of FIG. 3 positioned within the first section of the digestive tract and the stapling head assembly of FIG. 4 positioned within the separate second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) of anvil (400) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (not shown) within user interface feature (114) of handle assembly (100) to determine whether the gap distance (d) between opposing surfaces (412, 322) of anvil (400) and stapling head assembly (300) is appropriate; and make any necessary adjustments via knob (130).

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing firing trigger (150) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally together, as shown in FIG. 7D.

As knife member (340) translates distally, cutting edge (342) of knife member (340) cuts excess tissue that is positioned within annular recess (418) of anvil (400) and the interior of knife member (340). Additionally, washer (417) positioned within annular recess (418) of anvil (400) is broken by knife member (340) when the knife member (340) completes a full distal range of motion from the position shown in FIG. 7C to the position shown in FIG. 7D. It should be understood that washer (417) may also serve as a cutting board for knife member (340) to assist in cutting of tissue.

Figure 7D:
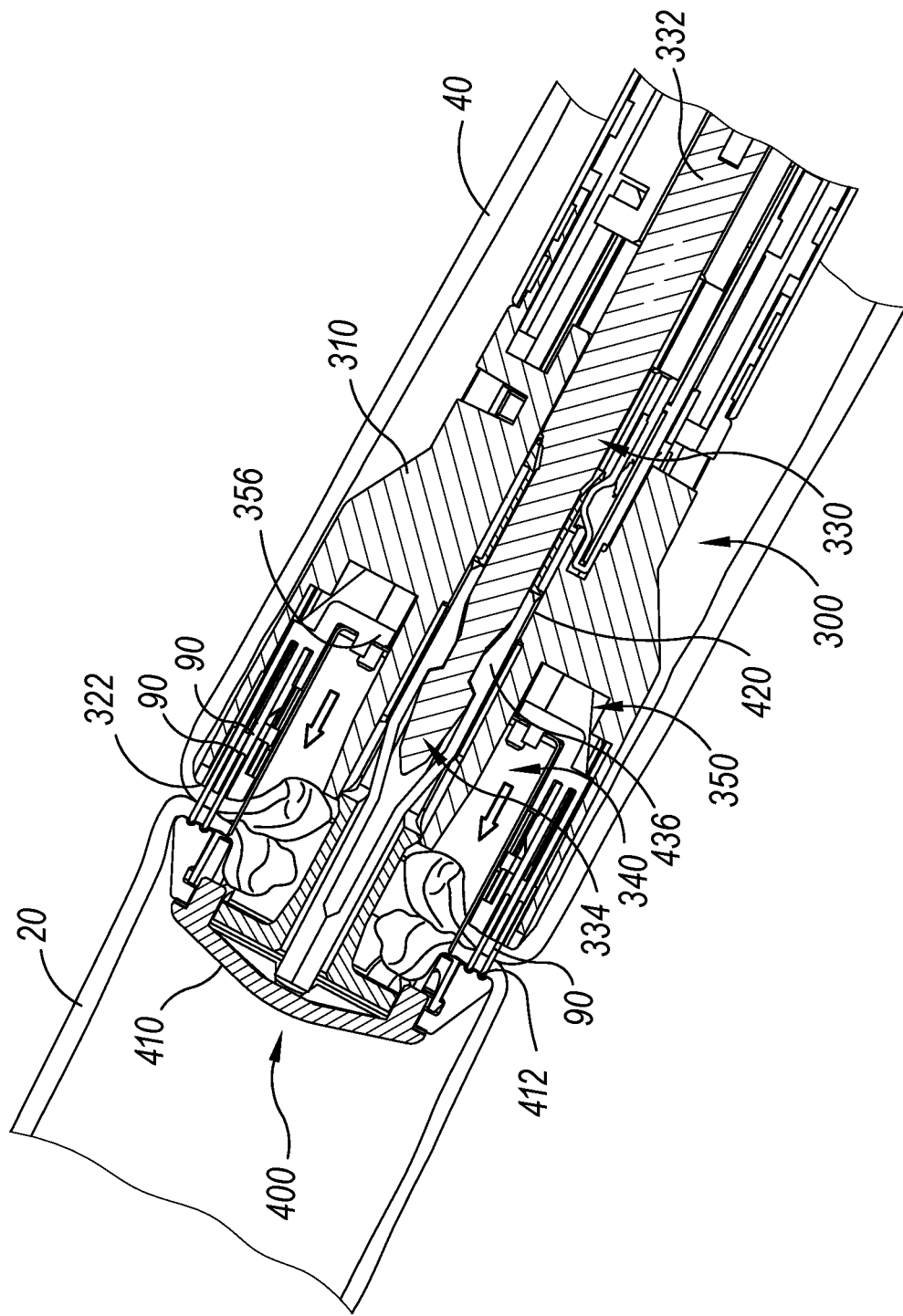
FIG. 7D depicts a cross-sectional side view of the anvil of FIG. 3 positioned within the first section of the digestive tract and the stapling head assembly of FIG. 4 positioned within the second section of the digestive tract, with the stapling head assembly actuated to sever and staple the clamped tissue and thereby joining the first and second sections of the digestive tract.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
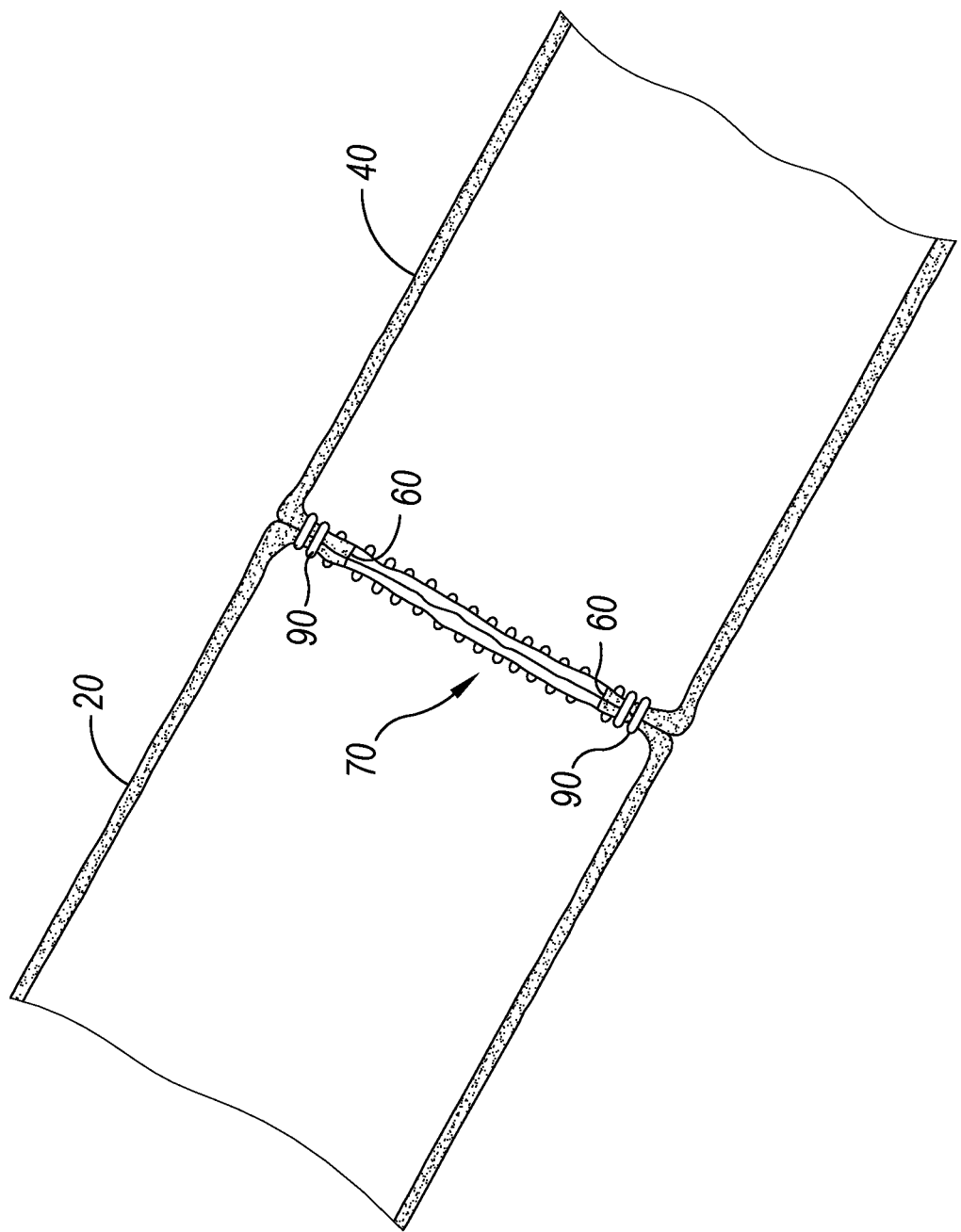
FIG. 7E depicts a cross-sectional side view of the first and second sections of the digestive tract of FIG. 7A joined together at an end-to-end anastomosis formed with the circular stapler of FIG. 1.

After the operator has actuated (or "fired") stapling head assembly (300) as shown in FIG. 7D, the operator rotates knob (130) to drive anvil (400) distally away from stapling head assembly (300), thereby increasing the gap distance (d) to facilitate release of the tissue between surfaces (412, 322). The operator then removes instrument (10) from the patient, with anvil (400) still secured to trocar (330). With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. Exemplary End Effector with Staple Line Alignment Feature

In some procedures where an anastomosis is created, one or more structures with a lumen may be transected where a linear sealing and transection staple line is formed in the tissue structure. By way of example only, and not limitation, in procedures such as sigmoid colectomy or lower anterior resection, two linear sealing and transection staple lines are formed as a step. One transection staple line is in the descending upper colon and one in the lower colon.

When creating the anastomosis in these exemplary procedures, at least one of these transection staple lines will interact with the circular staple pattern because it is necessary to cut through and staple over portions of at least one of the transection staple lines. For instance, in some versions of these procedures the transection staple line in the descending upper colon can be avoided when creating the anastomosis by creating a "J" pouch and putting the anvil of the stapler into the side of the colon above this upper transection staple line. However, in this example the lower transection staple line will be stapled into the anastomosis since it is practical to place the staple cartridge directly at the end of the sealed lower colon during an anastomosis procedure.

To create the anastomosis with acceptable sealing and integrity, it can be desirable to try to minimize the interaction between the linear transection staples and the staples deployed in the annular pattern. In exemplary versions that will be described further below, alignment features can be incorporated into the end effector to help minimize these staple-to-staple interactions. In doing so, a better balance between stapled and unstapled compressed tissue may be achieved. Also, these alignment features may aid in preventing the transection linear staple line from interfering with the stretch of the anastomotic staple line. Furthermore, these alignment features may allow operators using the stapler to better plan and control the twist and local tissue tension around the so-called "dog ears" that represent tissue mass adjacent to the stapled intersection of the transection staple and anastomotic staples. Still other benefits to using the alignment features described herein will be apparent to those of ordinary skill in the art in view of the teachings herein.

A. Exemplary Stapling Head Assembly and Anvils

Figure 8:
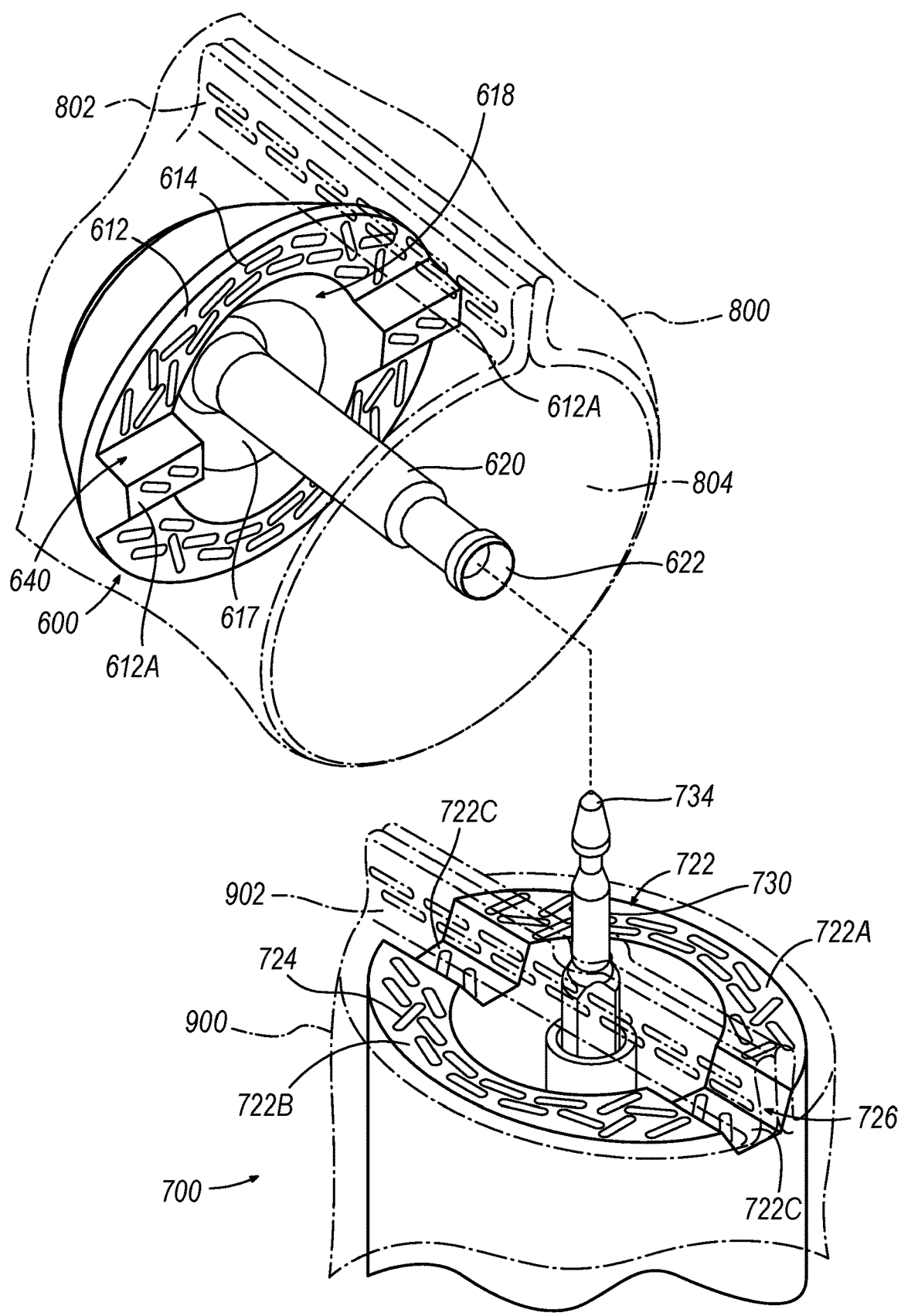
FIG. 8 depicts a perspective view of an alternate anvil and stapling head assembly, including staple line alignment features, for use with the circular stapler of FIG. 1.

Referring to FIG. 8, an exemplary anvil (600) is shown separate from an exemplary portion of a stapling head assembly (700). Anvil (600) and stapling head assembly (700) are usable with instrument (10). For instance, in some versions, instrument (10) is fit with stapling head assembly (700) in place of stapling head assembly (300) described above. Furthermore, instrument (10) can be fit with anvil (600) in place of anvil (400) described above.

In the present example, anvil (600) is shown positioned within a tubular anatomical structure or lumen (800), shown in phantom. Tubular anatomical structure (800) is sealed with a transecting staple line (802). In the present example, transecting staple line (802) initially represented a distal end of tubular anatomical structure (800). However, to avoid a proximal stapling surface (612) of anvil (600) interacting with transecting staple line (802) when forming an anastomosis, tubular anatomical structure (800) is oriented in a "J" shape with staple line (802) moved proximally and laterally so that proximal stapling surface (612) of anvil (600) contacts a sidewall (804) within tubular anatomical structure (800) when forming an anastomosis.

In the present example, stapling head assembly (700) is shown positioned with a tubular anatomical structure or lumen (900), shown in phantom. Tubular anatomical structure (900) is sealed with a transecting staple line (902). As shown, stapling head assembly (700) includes coupling member (730) that extends through transecting staple line (902). Coupling member (730) is configured to couple with a coupling member (620) of anvil (600) in a similar fashion to that described above with respect to stapling head assembly (300) and anvil (400). Once anvil (600) and stapling head assembly (700) are coupled together, the anastomosis procedure continues as will be described further below.

FIG. 9 depicts annular deck member (720) of stapling head assembly (700). Annular deck member (720) comprises deck surface (722) that in the present example includes a first planar portion (722A), also referred to as a first portion, a second planar portion (722B), also referred to as a second portion, and a third portion (722C) between first and second planar portions (722A, 722B). In some versions, the first planar portion (722A) and the second planar portion (722B) are coplanar. In the present example, third portion (722C) is configured as an alignment feature (726) for aligning deck member (720) with transecting staple lines (902). Alignment feature (726) defines a groove with deck surface (722) where groove is configured to align with and receive tissue having transecting staple line (902). In the illustrated version, alignment feature (726) is non-coplanar with first planar portion (722A) and second planar portion (722B). When compressing the tissue of tubular anatomical structures (800, 900) when forming an anastomosis (as will be described further below), tissue with transecting staple line (902) rests below deck surface portions (722A, 722B) such that staple-to-staple interactions between transected staple line (902) and the anastomotic staples are minimized.

Figure 11:
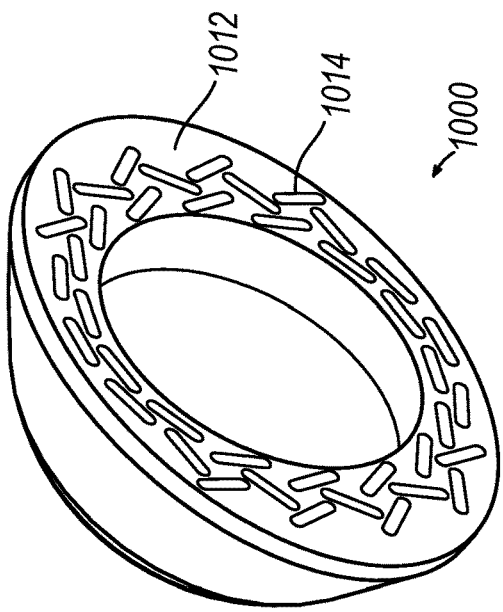
FIG. 11 depicts a perspective view of a portion of an alternate anvil similar to that shown in FIG. 10, but without an alignment feature component.
Figure 10:
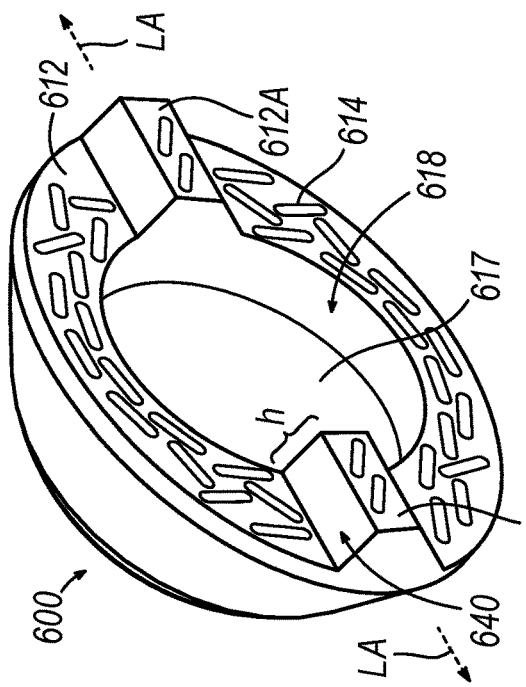
FIG. 10 depicts a perspective view of a portion of the anvil of FIG. 8.

FIGS. 10 and 11 depicts portions of respective anvils (600, 1000). As shown, both anvils (600, 1000) are shown without the coupling member that connects with coupling member (730) of stapling head assembly (700) so that proximal stapling surfaces (612, 1012) are more readily visible. Both anvils (600, 1000) have an oval shape as shown, and this oval shape matches the oval shape of annular deck member (720). Accordingly, the staple openings (724) of stapling head assembly (700) align with the staple forming pockets (614, 1014) of respective anvils (600, 1000) when stapling head assembly (700) is coupled with either anvil (600, 1000).

With anvil (600), a step feature (640) is included, whereas such a step feature is omitted from anvil (1000). Step feature (640) in the present example is configured as a raised portion that is sized and shaped to complement the groove configuration of alignment feature (726) of deck member (720). In some other versions, step feature (640) may be omitted as illustrated with anvil (1000), or step feature (640) could be configured as a recess rather than a raised portion. Furthermore, step feature (640) could have different heights (h) representing the degree to which step feature (640) is raised or protrudes away from proximal stapling surface (612) toward deck member (720), or the degree to which step feature is recessed in the case of a negative height (h). For example, in one version step feature (640) may be raised as shown, but sized such that, when aligned with deck member (720), step feature (640) assists in alignment by minimally engaging the groove of alignment feature (726) such that alignment feature (720) maintains its ability to receive and accommodate tissue with transecting staple line (902). In such a version, step feature (640) is meant to merely aid in aligning anvil (600) to the overall oval shape of deck member (720) of stapling head assembly (700). In such an example, the height (h) of stepped featured (640) is less than the depth of the groove defining alignment feature (726).

With deck member (720) and anvil (600), each have an oval shape, and accordingly each define a respective longitudinal axis (LA) that extends along the long dimension of the respective oval shapes. In the illustrated examples shown in FIGS. 8-10, alignment feature (726) of deck member (720) and stepped feature (640) of anvil (600) are oriented along respective longitudinal axes (LA). In other versions however, alignment feature (726) and stepped feature (640) may have other orientations relative to respective longitudinal axes (LA) of deck member (720) and anvil (600).

In some procedures, stapling head assemblies described herein, including e.g., stapling head assembly (700) and anvils described herein, including e.g., anvils (400, 600) can be arranged relative to other components of instrument (10) for ease of use of instrument (10). For example, in lower anterior resection, the transection linear staple line is often generally parallel to the plan of the patient's back. In this case, the orientation of alignment feature (726) and/or stepped feature (640) should line up to this such that their orientation is generally perpendicular to body assembly or handle assembly (100) of instrument (10). This orientation improves the ease of use of instrument (10) between the patient's legs. In view of the teachings herein, other procedure-specific orientations and configurations for instrument (10) having an end effector with one or more alignment features as described herein will be apparent to those of ordinary skill in the art.

B. Exemplary Anastomosis Procedure

FIGS. 12A-12D depict a series of partial section views showing portions of instrument (10) being used to form anastomosis (70) between two tubular anatomical structures (800, 900). By way of example only, tubular anatomical structures (800, 900) may comprise sections of a patient's esophagus, colon, or other portions of the patient's digestive tract, or any other tubular anatomical structures.

Figure 12A:
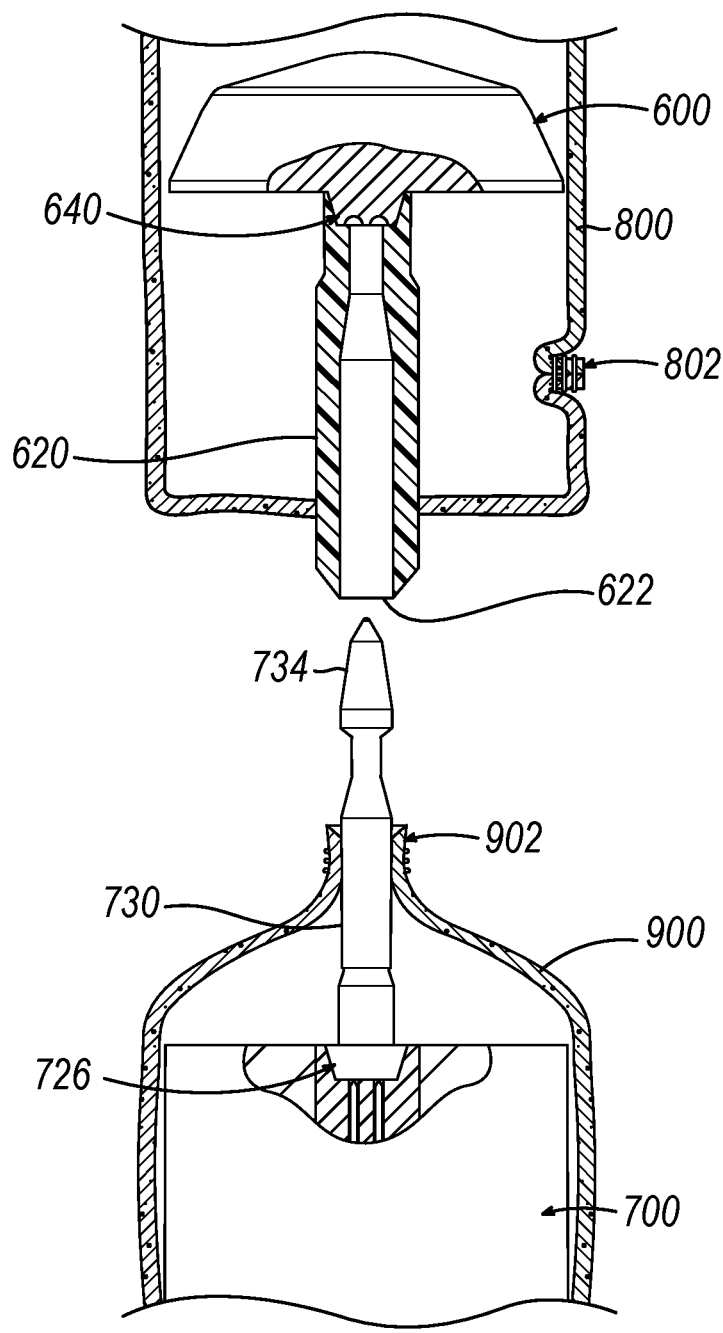
FIGS. 12A-12D depict a series view in partial cross section of the stapling head assembly of FIG. 8 used with the anvil of FIG. 11 to create an anastomosis.

As shown in FIG. 12A, anvil (600) is positioned in one tubular anatomical structure (800) and stapling head assembly (700) is positioned in another tubular anatomical structure (900). Anvil (600) is positioned in tubular anatomical structure (800) such that coupling member (620) punctures and protrudes from sidewall (804) of tubular anatomical structure (800). In some other versions, coupling member (620) does not puncture sidewall (804). Instead, it merely contacts the interior of sidewall (804) and subsequently connects with coupling member (730) of stapling head assembly (700), which punctures sidewall (804) from the exterior. In the present example, and as mentioned above, transection staple line (802) is shown to the side using the "J" pouch technique described above to eliminate staple-to-staple interactions between the staples of transection staple line (802) and the staples to be deployed in forming the anastomosis.

Stapling head assembly (700) is positioned in tubular anatomical structure (900) such that coupling member (730) punctures and protrudes from the stapled end of tubular anatomical structure (900) shown by transection staple line (902). Stapling head assembly (700) is then urged distally to ensure that stapling head assembly (700) is fully seated near the distal end of tubular anatomical structure (900) with coupling member (730) visible on the exterior of tubular anatomical structure (900).

Figure 12B:
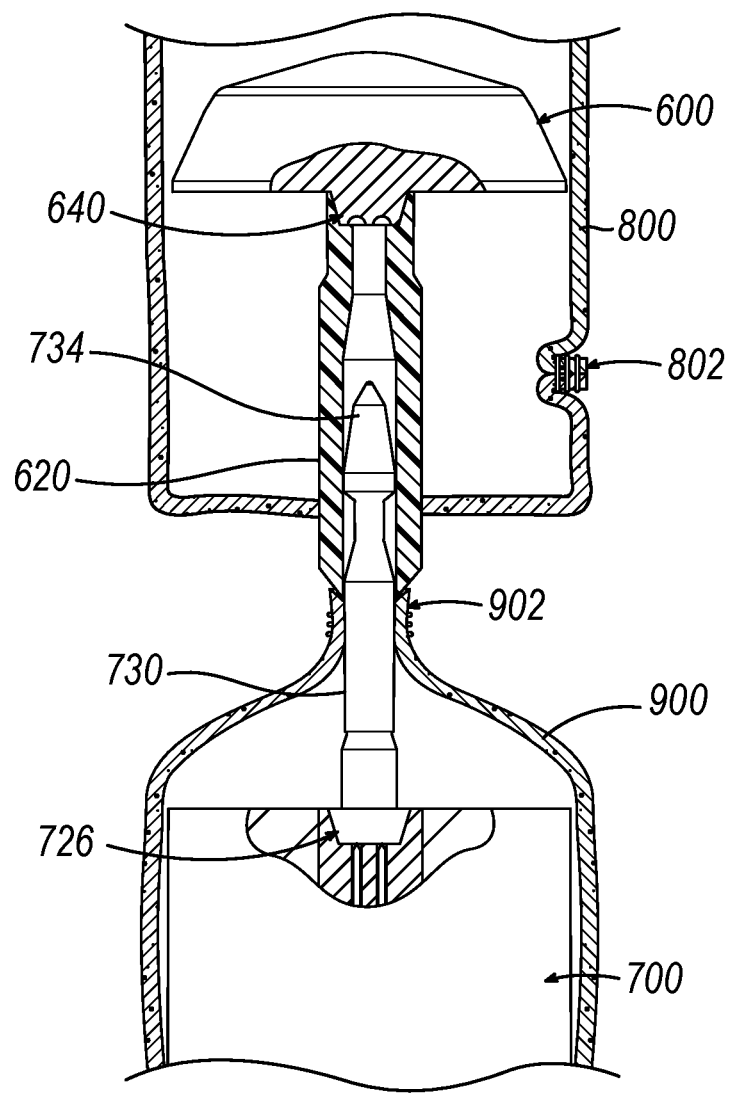
Figure 12C:
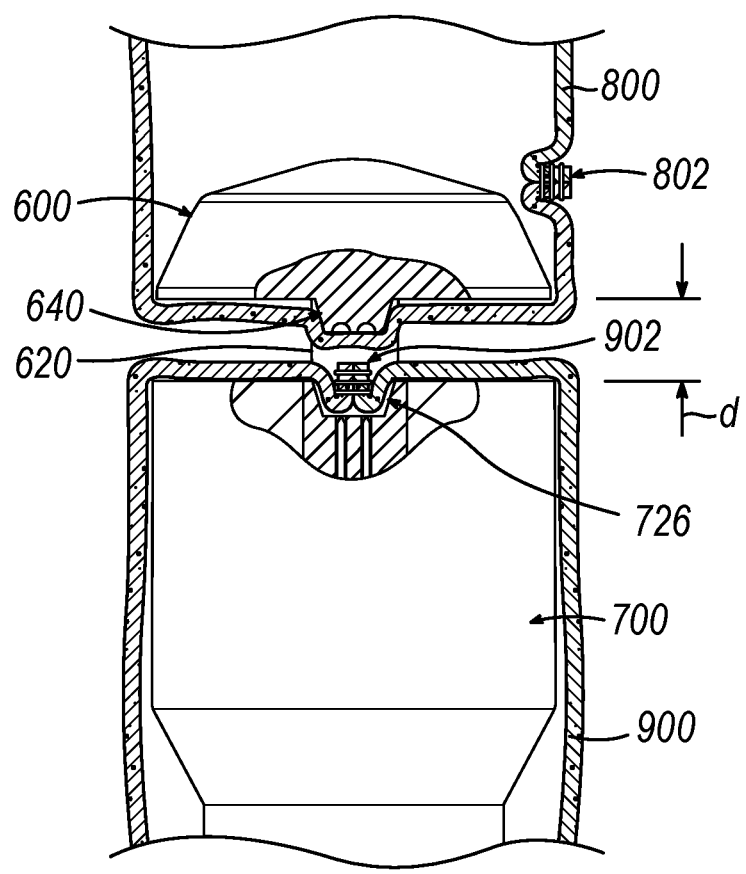

Next, anvil (600) is secured to coupling member (730) by inserting coupling member (730) into a bore (622) of coupling member (620) as shown in FIG. 12B. Latch members (not shown, but similar to latch members (430) described above) of anvil (600) engage a head (734) of coupling member (730), thereby providing a secure fit between anvil (600) and coupling member (730). The operator then rotates knob (130) of instrument (10) while holding casing (110) stationary via pistol grip (112). This rotation of knob (130) causes coupling member (730) and anvil (600) to retract proximally toward deck member (720) as shown in FIG. 12C. With stapling head assembly (700) at the distal end of tubular anatomical structure (900), alignment feature (726) aligns with transection staple line (902) and receives transection staple line (902) within the groove or recess defined by alignment feature (726) as shown in FIG. 12C.

Figure 12D:
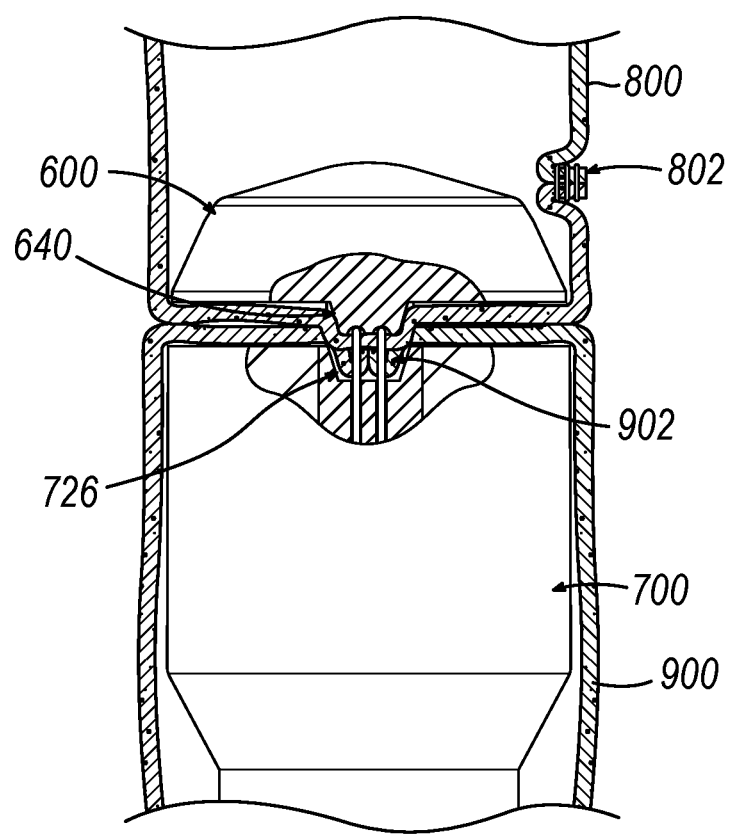

As shown in FIG. 12D, further proximal retraction of coupling member (730) and anvil (600) compresses the tissue of tubular anatomical structures (800, 900) between surfaces (612, 722) of anvil (600) and stapling head assembly (700). As this occurs, the operator may observe the tactile resistance or feedback via knob (130) while turning knob (130), with such tactile resistance or feedback indicating that the tissue is being compressed. Additionally, the operator may observe the tactile feedback of step feature (640) aligning with alignment feature (726) such that the oval shapes of anvil (600) and stapling head assembly (700) align for complete overlapping coverage where stapling openings (724) align with respective corresponding staple forming pockets (614). As the tissue is being compressed, the operator may visually observe the position of an indicator needle (522) within user interface feature (114) of handle assembly (100) to determine whether the gap distance (d) between opposing surfaces (612, 722) of anvil (600) and stapling head assembly (700) is appropriate; and make any necessary adjustments via knob (130).

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing firing trigger (150) to actuate the switch of motor activation module (180) and thereby activate motor (160) to rotate. This rotation of motor (160) causes actuation (or "firing") of stapling head assembly (700) by actuating drive bracket (250) distally to thereby drive knife member (not shown) and staple driver member (not shown) distally together. As knife member translates distally, excess tissue that is positioned within annular recess (618) of anvil (600) and the interior of knife member is cut. Additionally, washer (617) positioned within annular recess (618) of anvil (600) is broken by knife member when the knife member completes a full distal range of motion. It should be understood that washer (617) may also serve as a cutting board for knife member to assist in cutting of tissue.

As staple driver member (not shown) translates distally, staple driver member drives staples (90) through the tissue of tubular anatomical structures (800, 900) and into staple forming pockets (614) of anvil (600). Staple forming pockets (614) deform the driven staples (90) into a "B" shape or a three-dimensional shape, for example, such that the formed staples (90) secure the ends of tissue together, thereby coupling tubular anatomical structure (800) with tubular anatomical structure (900).

After the operator has actuated (or "fired") stapling head assembly (700) as shown, the operator rotates knob (130) to drive anvil (600) distally away from stapling head assembly (700), thereby increasing the gap distance (d) to facilitate release of the tissue between surfaces (612, 722). The operator then removes instrument (10) from the patient, with anvil (600) still secured to coupling member (730). With instrument (10) removed, the tubular anatomical structures (800, 900) are left secured together by two annular arrays of staples (90) at an anastomosis (70). The inner diameter of the anastomosis (70) is defined by the severed edge (60) left by the knife member.

C. Exemplary Alternate Shaped Stapling Head Assemblies and Anvils

Figure 13:
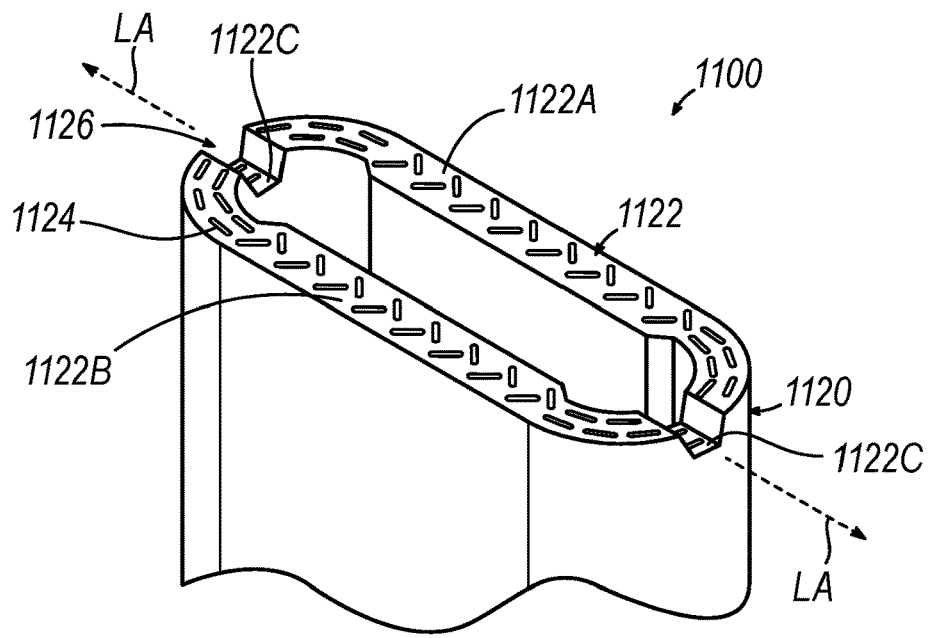
FIG. 13 depicts a perspective view of an alternate exemplary annular deck member of a stapling head assembly with the annular deck member having a dog-bone shape and an alignment feature.
Figure 14:
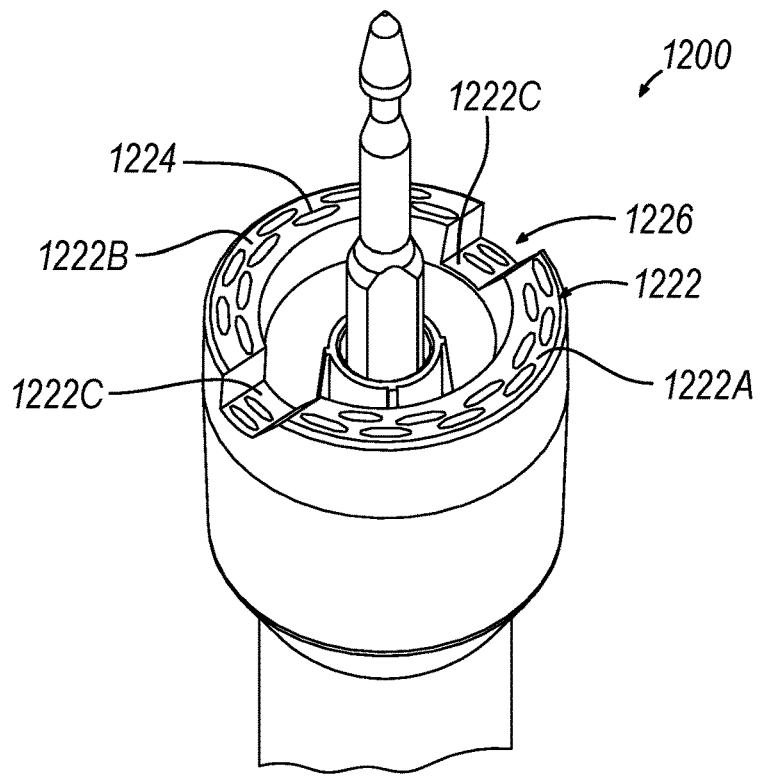
FIG. 14 depicts a perspective view of an alternate exemplary stapling sigmoid colectomy head assembly having a circular shape with an alignment feature.

FIGS. 13 and 14 depict portions of stapling head assemblies (1100, 1200), which have respective deck members (1120, 1220) that incorporate respective alignment features (1126, 1226) similar to alignment feature (726) described above. As shown with respective to stapling head assembly (1100) of FIG. 13, deck member (1120) of stapling head assembly (1100) is dog-bone shaped with an elongated curved shape. In this manner deck member (1120) defines a longitudinal axis (LA) along its long dimension. In the present example, alignment feature (1126) is oriented along this longitudinal axis (LA). Stapling head assembly (1100) is shown without coupling member (730) to clearly illustrate the shape of deck member (1120). It is understood that stapling head assembly (1100) includes all the corresponding components described with respect to stapling head assembly (300) above, those components being adapted to accommodate the dog-bone shape of deck member (1120). Furthermore, stapling head assembly (1100) is usable with instrument (10) by replacing stapling head assembly (300) with stapling head assembly (1100). In doing so a matching anvil (not shown) that has a corresponding dog-bone shape to deck member (1120) would be used with instrument (10) in place of anvil (400). Accordingly, the staple openings (1124) of stapling head assembly (1100) would align with the staple forming pockets of the respective anvil when stapling head assembly (1100) is coupled with the corresponding anvil.

Similar to alignment feature (726), alignment feature (1126) defines a groove within deck surface (1122). Deck surface (1122) includes a first planar portion (1122A), a second planar portion (1122B), and a third portion (1122C) between first and second planar portions (1122A, 1122B). In the present example, third portion (1122C) is configured as alignment feature (1126) for aligning deck member (1120) with transecting staple lines (902). For example, the groove defined by alignment feature (1126) is configured to align with and receive tissue having transecting staple line (902). In this manner, when compressing the tissue of tubular anatomical structures (800, 900) when forming an anastomosis (as described above), tissue with transecting staple line (902) rests below deck surface portions (1122A, 1122B) such that staple-to-staple interactions between transected staple line (902) and the anastomotic staples are minimized.

As shown with respective to stapling head assembly (1200) of FIG. 14, deck member (1220) of stapling head assembly (1200) is circular shaped. In this manner deck member (1120) defines a diameter. In the present example, alignment feature (1126) is oriented along the diameter of the circular shaped deck member (1220). Stapling head assembly (1200) is shown with coupling member (730), which would couple to an anvil's coupling member such as anvil (400) and its coupling member or shank (420). It is understood that stapling head assembly (1200) includes all the corresponding components described with respect to stapling head assembly (300) above, those components being adapted to accommodate the alignment feature (1226) of deck member (1220). Furthermore, stapling head assembly (1200) is usable with instrument (10) by replacing stapling head assembly (300) with stapling head assembly (1200). In doing so a matching circular anvil with a stepped feature like stepped feature (640) described above (not shown) would be used with instrument (10) in place of anvil (400). In another version though, circular shaped anvil (400) without a stepped feature, as described above, can also be used with stapling head assembly (1200) with instrument (10). In either case, the staple openings (1224) of stapling head assembly (1200) would align with the staple forming pockets of the respective anvil when stapling head assembly (1200) is coupled with the anvil.

Similar to alignment feature (726), alignment feature (1226) defines a groove within deck surface (1222). Deck surface (1222) includes a first planar portion (1222A), a second planar portion (1222B), and a third portion (1222C) between first and second planar portions (1222A, 1222B). In the present example, third portion (1222C) is configured as alignment feature (1226) for aligning deck member (1220) with transecting staple lines (902). For example, the groove defined by alignment feature (1226) is configured to align with and receive tissue having transecting staple line (902). In this manner, when compressing the tissue of tubular anatomical structures (800, 900) when forming an anastomosis (as described above), tissue with transecting staple line (902) rests below deck surface portions (1222A, 1222B) such that staple-to-staple interactions between transected staple line (902) and the anastomotic staples are minimized. While dog-bone, oval, and circular shaped stapling head assemblies and anvils having alignment features are described herein, other shaped structures for these may be used and will be apparent to those of ordinary skill in the art. Additionally, further exemplary oval and dog-bone shaped stapler end effectors are shown and described in U.S. patent application Ser. No. 17/401,428, entitled "Staple Forming Features for Circular Surgical Stapler," filed on Aug. 13, 2021, issued as U.S. Pat. No. 11,998,209 on Jun. 4, 2024; and U.S. patent application Ser. No. 17/401,430, entitled "Non-Circular End Effector Features for Circular Surgical Stapler," filed on Aug. 13, 2021, issued as U.S. Pat. No. 11,944,310 on Apr. 2, 2024. The disclosures of each are incorporated by reference herein.

D. Exemplary Tissue Gaps and Staple Configurations

As described above, deck surface (722) of deck member (720) has first and second planar portions (722A, 722B) and third portion (722C). In one version, third portion (722C) is not coplanar with first and second portions (722A, 722B). As also mentioned above, the tissue gap or gap distance (d) represents the distance between deck surface (722) and proximal stapling surface (412, 612) of anvil (400, 600). In versions of instrument (10) using stapling head assembly (700) with anvil (400), gap distance (d) is non-uniform across the end effector as there is a greater distance between the surfaces of anvil (400) and deck member (720) at third portion (722C) defining alignment feature (726) compared to the distance at first and second planar portions (722A, 722B). This is the case, because alignment feature (726) defines a groove that is recessed relative to first and second planar portions (722A, 722B).

Other versions of instrument (10) can incorporate alignment feature (726) or a similar alignment feature and also be paired with an anvil having a complementary stepped feature (640) or a similar complementary stepped feature. This could be the case, for instance, when instrument (10) includes stapling head assembly (700) and anvil (600). In these versions, the height (h) of stepped feature (640) relative to the depth of the recess or groove of alignment feature (726) will define gap distance (d) at third portion (722C). In some instances, gap distance (d) at third portion (722C) is the same as gap distance (d) at first and second planar portions (722A, 722B). In other versions, gap distance (d) at third portion (722C) is smaller or larger than gap distance (d) at first and second planar portions (722A, 722B). In view of the teachings herein, various other configurations of instrument (10) to achieve various gap distances (d) across the anvil and deck member surfaces will be apparent to those of ordinary skill in the art.

Figure 15A:
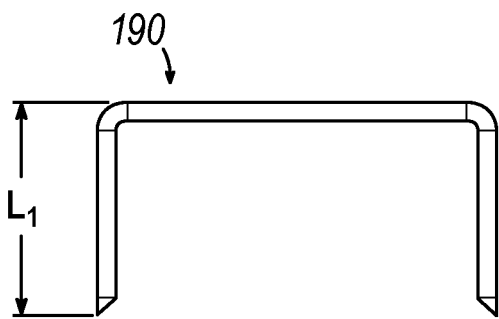
FIG. 15A depicts a front view of an exemplary staple having a first staple leg length, the staple usable with the various stapling head assemblies described herein.
Figure 15B:
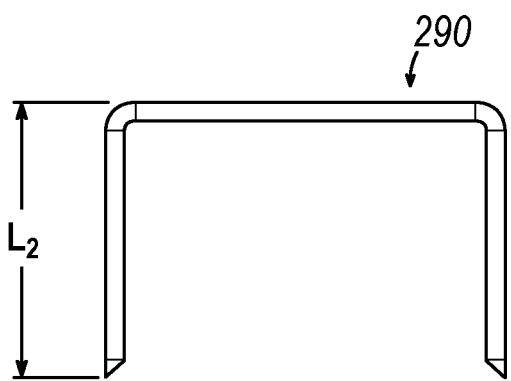
FIG. 15B depicts a front view of another exemplary staple having a second staple leg length, the staple usable with the various stapling head assemblies described herein.

In some versions with a non-uniform tissue gap or gap distance (d), staple geometry differs across deck surface (722) of deck member (720). For example, FIGS. 15A and 15B depict staples (190, 290) with each having a different unformed staple leg length. Staple (190) has an unformed staple leg length (L1) that is shorter than unformed staple leg length (L2) of staple (290). In one version, staples (290) with their longer unformed staple leg length (L2) are used with stapling head assembly (700) at third portion (722C) where alignment feature (726) is located. At the other first and second planar portions (722A, 722B), staples (190) with their shorter unformed staple leg length (L1) are used. In such an example, the staples with the longer unformed staple leg length provide improved stapling performance at the areas there the transection line staples interact with the anastomotic staples. For example, the longer unformed staple leg length staples can provide more secure integration of the staple lines and minimize leaks around the dog ears. In some other instances, staples (190) may be used at third portion (722C) instead, and staples (290) used at first and second planar portions (722A, 722B). For instance, this could be helpful in minimizing staple-to-staple interactions at the overlap of transection line staples and anastomotic staples. The nature of the tissue being stapled as well as the configuration of the transection line staples may inform the operator as to which stapling configuration is desired when using staples of differing unformed staple leg lengths.

Figure 16A:
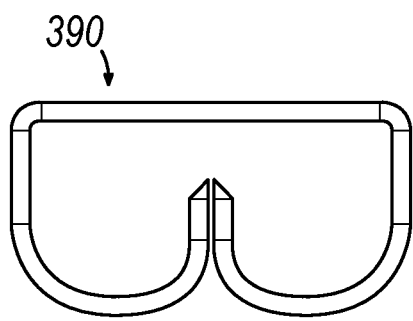
FIG. 16A depicts a front view of an exemplary staple having a first wire diameter, the staple usable with the various stapling head assemblies described herein.
Figure 16B:
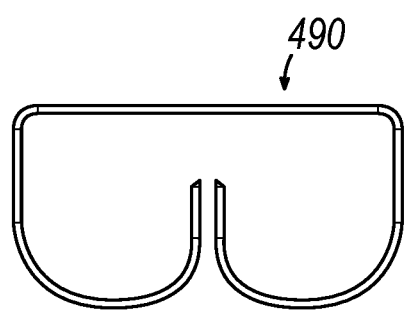
FIG. 16B depicts a front view of an exemplary staple having a second wire diameter, the staple usable with the various stapling head assemblies described herein.

FIGS. 16A and 16B depict staples (390, 240) with each having a different staple wire size or diameter. Staple (390) has a staple wire size that is larger than the staple wire size of staple (490). In one version, staples (390) with their larger wire size are used with stapling head assembly (700) at third portion (722C) where alignment feature (726) is located. At the other first and second planar portions (722A, 722B), staples (490) with their smaller wire size are used. In such an example, the staples with the larger wire size provide improved stapling performance at the areas there the transection line staples interact with the anastomotic staples. For example, the staples with the larger wire size or diameter can provide more secure integration of the staple lines and minimize leaks around the dog ears. In some other instances, staples (490) may be used at third portion (722C) instead, and staples (390) used at first and second planar portions (722A, 722B). For instance, this could be helpful in minimizing staple-to-staple interactions at the overlap of transection line staples and anastomotic staples. The nature of the tissue being stapled as well as the configuration of the transection line staples may inform the operator as to which stapling configuration is desired when using staples of differing wire size.

Figure 17A:
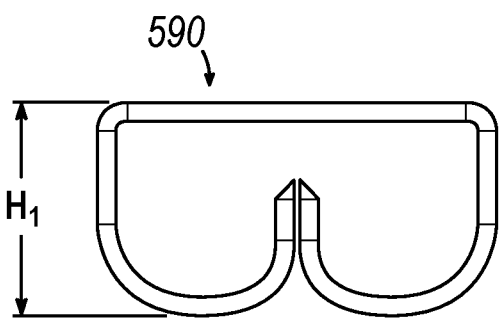
FIG. 17A depicts a front view of an exemplary staple having a first formed staple height, the staple usable with the various stapling head assemblies described herein.
Figure 17B:
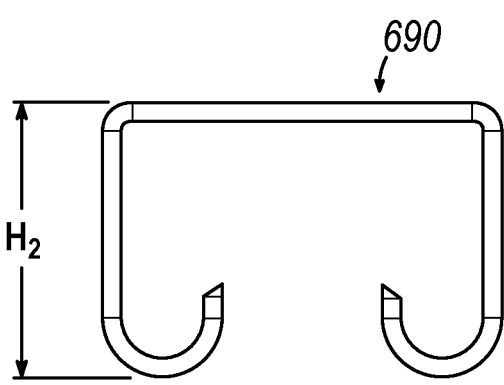
FIG. 17B depicts a front view of an exemplary staple having a second formed staple height, the staple usable with the various stapling head assemblies described herein.

FIGS. 17A and 17B depict staples (590, 690) with each having a different formed staple height. Staple (590) has an unformed staple height (H1) that is shorter than formed staple height (H2) of staple (690). In one version, staples (690) with their longer formed staple height (H2) are used with stapling head assembly (700) at third portion (722C) where alignment feature (726) is located. At the other first and second planar portions (722A, 722B), staples (590) with their shorter formed staple height (H1) are used. In such an example, staples (690) with their greater formed staple height provide improved stapling performance at the areas there the transection line staples interact with the anastomotic staples. For example, the staples with the larger formed staple height can provide more secure integration of the staple lines and minimize leaks around the dog ears. In some other instances, staples (590) may be used at third portion (722C) instead, and staples (690) used at first and second planar portions (722A, 722B). For instance, this could be helpful in minimizing staple-to-staple interactions at the overlap of transection line staples and anastomotic staples. The nature of the tissue being stapled as well as the configuration of the transection line staples may inform the operator as to which stapling configuration is desired when using staples of differing formed staple heights.

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus for creating an anastomosis between two lumens, comprising: (a) a body; (b) a shaft extending distally from the body; (c) a stapling head assembly positioned at a distal end of the shaft, wherein the stapling head assembly includes: (i) an annular deck member, wherein the annular deck member includes: (A) a deck surface configured to contact a tissue defining a select one of the two lumens, (B) an annular array of staple openings formed through the deck surface, and (C) an alignment feature configured to align the deck surface of the deck member with a linear feature of the tissue defining the select one of the two lumens; (ii) a staple driver operable to drive staples through the annular array of staple openings; and (d) an anvil configured to deform the staples driven by the staple driver to form a ring-shaped staple pattern configured to connect the two lumens.

EXAMPLE 2

The apparatus of Example 1, wherein the annular deck member comprises a circular shape.

EXAMPLE 3

The apparatus of Example 1, wherein the annular deck member comprises an oval shape.

EXAMPLE 4

The apparatus of Example 1, wherein the annular deck member comprises a dog-bone shape.

EXAMPLE 5

The apparatus of any one or more of Example 1 through Example 4, wherein deck member comprises a shape defining a longitudinal axis and the alignment feature is oriented along the longitudinal axis.

EXAMPLE 6

The apparatus of any one or more of Example 1 through Example 5, wherein the linear feature of the tissue comprises a staple line transecting the select one of the two lumens closing an open end of the select one of the two lumens.

EXAMPLE 7

The apparatus of any one or more of Example 1 through Example 6, wherein the alignment feature is defined by a portion of the deck surface.

EXAMPLE 8

The apparatus of any one or more of Example 1 through Example 7, wherein the alignment feature comprises a groove in the deck surface.

EXAMPLE 9

The apparatus of any one or more of Example 1 through Example 8, wherein the alignment feature is oriented orthogonal to a longitudinal axis defined by the body.

EXAMPLE 10

The apparatus of any one or more of Example 1 through Example 9, wherein the anvil comprises a stapling surface, wherein a distance between the stapling surface of the anvil and the deck surface of the deck member of the stapling head assembly defines a gap, wherein the gap is non-uniform due to the presence of the alignment feature.

EXAMPLE 11

The apparatus of Example 10, wherein the gap at the alignment feature is larger than the gap elsewhere.

EXAMPLE 12

The apparatus of any one or more of Example 1 through Example 11, wherein the anvil comprises a complementary feature to the alignment feature.

EXAMPLE 13

The apparatus of Example 12, wherein the complementary feature of the anvil comprises a stepped feature and the alignment feature of the deck member comprises a groove in the deck surface.

EXAMPLE 14

The apparatus of any one or more of Example 1 through Example 13, wherein the deck surface of the deck member comprises a first portion and a second portion, wherein the alignment feature separates the first portion and the second portion.

EXAMPLE 15

The apparatus of Example 14, wherein the first portion and the second portion are each planar.

EXAMPLE 16

The apparatus of any one or more of Example 14 through Example 15, wherein the first portion and the second portion are coplanar, and the alignment feature is non-coplanar with the first portion and the second portion.

EXAMPLE 17

An apparatus for creating an anastomosis between two lumens, comprising: (a) a body; (b) a shaft extending distally from the body; (c) a stapling head assembly positioned at a distal end of the shaft, wherein the stapling head assembly includes: (i) an annular deck member, wherein the annular deck member includes: (A) a deck surface configured to contact a tissue defining a select one of the two lumens, wherein the deck surface comprises a first portion, a second portion, and a third portion, wherein the third portion defines an alignment feature separating the first and the second portions, wherein the alignment feature is configured to align the deck surface of the deck member with a linear feature of the tissue defining the select one of the two lumens, (B) an annular array of staple openings formed through the deck surface, wherein the annular array of staple openings includes a first region of staple openings located along the first and the second portions of the deck surface, and a second region of staple openings located along the third portion of the deck surface, (C) a first plurality of staples configured to travel through the first region of staple openings of the annular array of staple openings, and (D) a second plurality of staples configured to travel through the second region of staple openings of the annular array of staple openings, wherein the second plurality of staples differ in configuration from the first plurality of staples; (ii) a staple driver operable to drive the first and the second pluralities of staples through the annular array of staple openings; and (d) an anvil configured to deform the staples driven by the staple driver to form a ring-shaped staple pattern configured to connect the two lumens.

EXAMPLE 18

The apparatus of Example 17, wherein the second plurality of staples comprises a different staple leg length or staple wire diameter compared to the first plurality of staples.

EXAMPLE 19

The apparatus of any one or more of Example 17 through Example 18, wherein the second plurality of staples comprise a different full height form than the first plurality of staples.

EXAMPLE 20

A method of creating an anastomosis, the method comprises the steps of: (a) positioning an anvil of a surgical stapling instrument within a first lumen; (b) positioning a stapling head assembly of the surgical stapling instrument within a second lumen, the stapling head assembly including an annular deck member with a deck surface having an annular array of staple openings formed through the deck surface, an alignment feature configured to align the deck surface with a staple line transecting the second lumen, and a staple driver operable to drive staples through the annular array of staple openings; (c) aligning the alignment feature of the deck surface with the staple line transecting the second lumen; (d) connecting a first coupling member of the anvil with a second coupling member of the stapling head assembly; (e) compressing a tissue between the anvil and the deck surface; and (f) actuating the surgical stapling instrument to cut and staple the tissue while the staple line transecting the second lumen is located within the alignment feature.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Additionally, any one or more of the teachings herein may be combined with any one or more of the teachings of U.S. patent application Ser. No. 17/401,391, entitled "Methods of Forming an Anastomosis Between Organs with an Expandable Staple Pattern," filed on Aug. 13, 2021, published as U.S. Pub. No. 2023/0051305 on Feb. 16, 2023; U.S. patent application Ser. No. 17/401,428, entitled "Staple Forming Features for Circular Surgical Stapler," filed on Aug. 13, 2021, issued as U.S. Pat. No. 11,998,209 on Jun. 4, 2024; U.S. patent application Ser. No. 17/401,430, entitled "Non-Circular End Effector Features for Circular Surgical Stapler," filed on Aug. 13, 2021, issued as U.S. Pat. No. 11,944,310 on Apr. 2, 2024; U.S. patent application Ser. No. 17/401,444, entitled "Circular Surgical Stapler for Forming Pattern of Non-Tangential Staples," filed on Aug. 13, 2021, issued as U.S. Pat. No. 11,653,926 on May 23, 2023; U.S. patent application Ser. No. 17/401,451, entitled "Circular Surgical Stapler Having Staples with Expandable Crowns," filed on Aug. 13, 2021, issued as U.S. Pat. No. 11,911,039 on Feb. 27, 2024; and U.S. patent application Ser. No. 17/401,460, entitled "Circular Surgical Stapler for Forming Cross-Pattern of Staples," filed on Aug. 13, 2021, issued as U. S. Pat. No. 11,666,339 on Jun. 6, 2023. The disclosure of each of these US patent documents is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for creating an anastomosis between two lumens, comprising:
   (a) a body;
   (b) a shaft extending distally from the body;
   (c) a stapling head assembly positioned at a distal end of the shaft, wherein the stapling head assembly includes:
      (i) an annular deck member defining a dog-bone shape, wherein the annular deck member includes:
         (A) a deck surface configured to contact a tissue defining a select one of the two lumens, wherein the deck surface includes a width that extends transversely to a central axis of the stapling head assembly, wherein the deck surface of the deck member comprises a first portion and a second portion,
         (B) an annular array of staple openings formed through the deck surface, and
         (C) an alignment feature configured to align the deck surface of the deck member with a linear feature of the tissue defining the select one of the two lumens, wherein the alignment feature extends the width of the deck surface and transversely to the central axis to thereby define a plane extending along the width, wherein the alignment feature separates the first portion and the second portion;

(ii) a staple driver operable to drive staples through the annular array of staple openings; and (d) an anvil configured to deform the staples driven by the staple driver to form an annular staple pattern configured to connect the two lumens.

2. The apparatus of claim 1, wherein the annular deck member further comprises a circular shape.

3. The apparatus of claim 1, wherein the annular deck member further comprises an oval shape.

4. The apparatus of claim 1, wherein the dog-bone shape defines a longitudinal axis and the alignment feature is oriented along the longitudinal axis.

5. The apparatus of claim 1, wherein the linear feature of the tissue comprises a staple line transecting the select one of the two lumens closing an open end of the select one of the two lumens.

6. The apparatus of claim 1, wherein the alignment feature is defined by a portion of the deck surface.

7. The apparatus of claim 1, wherein the alignment feature comprises a groove in the deck surface.

8. The apparatus of claim 1, wherein the alignment feature is oriented orthogonal to a longitudinal axis defined by the body.

9. The apparatus of claim 1, wherein the anvil comprises a stapling surface, wherein a distance between the stapling surface of the anvil and the deck surface of the deck member of the stapling head assembly defines a gap, wherein the gap is non-uniform due to the presence of the alignment feature.

10. The apparatus of claim 9, wherein the gap at the alignment feature is larger than the gap elsewhere and is consistent across the width.

11. The apparatus of claim 1, wherein the anvil comprises a complementary feature to the alignment feature.

12. The apparatus of claim 11, wherein the complementary feature of the anvil comprises a stepped feature and the alignment feature of the deck member comprises a groove in the deck surface.

13. The apparatus of claim 1, wherein the first portion and the second portion are each planar.

14. The apparatus of claim 1, wherein the first portion and the second portion are coplanar, and the alignment feature is non-coplanar with the first portion and the second portion.

15. An apparatus for creating an anastomosis between two lumens, comprising:

(a) a body;

(b) a shaft extending distally from the body and including a longitudinal axis;

(c) a stapling head assembly positioned at a distal end of the shaft, wherein the stapling head assembly includes:

(i) an annular deck member defining a dog-bone shape, wherein the annular deck member includes:

(A) a deck surface configured to contact a tissue defining a select one of the two lumens, wherein the deck surface comprises a first portion, a second portion, and a third portion, wherein the third portion defines an alignment feature separating the first and the second portions, wherein the alignment feature is configured to align the deck surface of the deck member with a linear feature of the tissue defining the select one of the two lumens, (B) an annular array of staple openings formed through the deck surface, wherein the annular array of staple openings includes a first region of staple openings located on the first and the second portions of the deck surface, and a second region of staple openings located on the third portion of the deck surface, (C) a first plurality of staples configured to travel through the first region of staple openings of the annular array of staple openings, and (D) a second plurality of staples configured to travel through the second region of staple openings of the annular array of staple openings, wherein the second plurality of staples differ in configuration from the first plurality of staples; and (ii) a staple driver operable to drive the first and the second pluralities of staples through the annular array of staple openings; and (d) an anvil actuatable relative to the stapling head assembly between an open position and a closed position and configured to deform the staples driven by the staple driver to form an annular staple pattern configured to connect the two lumens, wherein in each of the open and closed positions a longitudinal distance between the anvil and the third portion is different than a longitudinal distance between the anvil and the first portion, wherein the longitudinal distance between the anvil and the third portion is consistent along a length of the third portion.

16. The apparatus of claim 15, wherein the second plurality of staples comprises a different staple leg length or staple wire diameter compared to the first plurality of staples.

17. The apparatus of claim 15, wherein the second plurality of staples comprise a different full height form than the first plurality of staples.

18. An apparatus for creating an anastomosis between two lumens, comprising:

(a) a body;

(b) a shaft extending distally from the body;

(c) a stapling head assembly positioned at a distal end of the shaft, wherein the stapling head assembly includes:

(i) an annular deck member defining a dog-bone shape, wherein the annular deck member includes:

(A) a deck surface configured to contact a tissue defining a select one of the two lumens, (B) an annular array of staple openings formed through the deck surface, and (C) an alignment feature configured to align the deck surface of the deck member with a linear fastening feature of the tissue defining the select one of the two lumens; and (ii) a staple driver operable to drive staples through the annular array of staple openings; and (d) an anvil configured to deform the staples driven by the staple driver to form an annular staple pattern configured to connect the two lumens, wherein the anvil includes a step, wherein the anvil is configured to transition between an open configuration and a closed configuration, wherein the anvil in the closed configuration is configured to compress the tissue against the annular deck member, wherein a gap between the step of the anvil and the alignment feature is configured to receive the linear fastening feature and is sized to accommodate a secured staple of the linear fastening feature while the anvil is in the closed configuration, wherein a staple opening opens into the gap.

* * * * *